(12) United States Patent
Ogawa et al.

(10) Patent No.: US 8,173,865 B2
(45) Date of Patent: May 8, 2012

(54) PLANT HAVING INCREASED YIELD OF SEEDS

(75) Inventors: Kenichi Ogawa, Kyoto (JP); Aya Iwasaki, Okayama (JP)

(73) Assignees: Japan Science and Technology Agency, Kawaguchi-Shi (JP); Okayama Prefecture, Okayama-Shi (JP)

( * ) Notice: Subject to any disclaimer, the term of this patent is extended or adjusted under 35 U.S.C. 154(b) by 171 days.

(21) Appl. No.: 12/523,283

(22) PCT Filed: Jan. 15, 2008

(86) PCT No.: PCT/JP2008/050341
§ 371 (c)(1),
(2), (4) Date: Jul. 15, 2009

(87) PCT Pub. No.: WO2008/087932
PCT Pub. Date: Jul. 24, 2008

(65) Prior Publication Data
US 2010/0083404 A1    Apr. 1, 2010

(30) Foreign Application Priority Data

Jan. 16, 2007    (JP) ................................. 2007-007464

(51) Int. Cl.
| | | |
|---|---|---|
| *A01H 1/00* | (2006.01) | |
| *A01H 5/00* | (2006.01) | |
| *A01H 5/10* | (2006.01) | |
| *C12N 15/82* | (2006.01) | |

(52) U.S. Cl. ........ 800/278; 800/290; 800/298; 435/410; 435/419; 435/468

(58) Field of Classification Search ........................ None
See application file for complete search history.

(56) References Cited

U.S. PATENT DOCUMENTS

| 7,479,267 B2 | 1/2009 | Ogawa et al. |
| 2009/0099023 A1 | 4/2009 | Ogawa et al. |

FOREIGN PATENT DOCUMENTS

| JP | 2001-190168 A | 7/2001 |
| JP | 2004-352679 A | 12/2004 |
| WO | WO-01/64928 A2 | 9/2001 |
| WO | WO-01/80638 A1 | 11/2001 |
| WO | WO 0210210 A2 * | 2/2002 |
| WO | WO-02/33105 A2 | 4/2002 |
| WO | WO 0233105 A2 * | 4/2002 |
| WO | WO-2004/061080 A2 | 7/2004 |

OTHER PUBLICATIONS

Noctor et al, Glutathione: biosynthesis, metabolism, and relationship to stress tolerance explored in transformed plants, 1998, Journal of Experimental Botany, 49:321, pp. 623-647.*

Xiang et al, Jun. 2001, Plant Physiology, vol. 126, pp. 564-574.*
Asada, et al., "Metabolism and Function of Glutathione in Plants," The Research Institute for Food Science, Kyoto University Extra Edition of Protein, Nucleic acid and Enzyme "An Epoch of Glutathione Research," vol. 33, No. 9, pp. 1513-1521 (1988)(and English translation).
Supplementary European Search Report (App No. EP 08 70 3205) as mailed Jul. 30, 2010.
Li, Yujing et al., "Arsenic and Mercury Tolerance and Cadmium Sensitivity in *Arabidopsis* Plants Expressing Bacterial γ-Glutamylcysteine Synthetase" Environmental Toxicology and Chemistry, vol. 24, No. 6, Jun. 2005, pp. 1376-1386.
Bittsanszky, Andras et al., "Ability of transgenic poplars with elevated glutathione content to tolerate zinc(2+) stress" Environment International 31, Feb. 2005, pp. 251-254.
International Search Report (PCT/ISA/220) for corresponding PCT/JP2008/050341.
Noctor, et al., "Glutathione:biosynthesis, metabolism and relationship to stress tolerance explored in transformed plants," Journal of Experimental Botany, 49:623-647 (1998).
Noctor, et al., "Synthesis of Glutathione in Leaves of Transgenic Poplar Overexpressing γ-Glutamylcysteine Synthetase" Plant Physiology, 112:1071-1078 (1996).
Noctor, et al., "Manipulation of Glutathione and Amino Acid Biosynthesis in the Chloroplast," 118:471-482 (1998).
Zhu, et al., "Cadmium Tolerance and Accumulation in Indian Mustard is Enhanced by Overexposing γ-Glutamylcysteine Synthetase," Plant Physiology, 121:1169-1177 (1999).
Creissen, et al., "Elevated Glutathione Biosynthetic Capacity in the Chloroplasts of Transgenic Tobacco Plants Paradoxically Causes Increased Oxidative Stress," The Plant Cell, 11: 1277-1291 (1999).
May, et al., "*Arabidopsis thaliana* γ-glutamylcysteine synthetase is Structurally Unrelated to Mammalian yeast, and *Escherichia coli* homologs" Proc. Natl. Acad. Sci., 91:10059-10063 (1994).
Ito, et al., "The Sugar-Metabolic Enzymes Aldolase and Triose-Phosphate Isomerase are Targets of Glutathionylation in *Arabidopsis thaliana*: Detection using Biotinylated Glutathione," Plant Cell Physiology, 44(7):655-660 (2003).
Xiang, et al., "The Biological Functions of Glutathione Revisited in *Arabidopsis* Transgenic Plants with Altered Glutathione Levels," Plant Physiology, 126:564-574 (2001).

* cited by examiner

*Primary Examiner* — Eileen B O Hara
(74) *Attorney, Agent, or Firm* — Edwards Wildman Palmer LLP; David G. Conlin; Lisa Swiszcz

(57) ABSTRACT

It is found that a transformed plant into which a γ-glutamylcysteine synthetase gene has been introduced is increased in at least one of the number of flowers and the number of seeds in comparison with a wild-type plant, and is therefore increased in seed yield. Based on this finding, the present invention elucidates the function of a product of a plant-derived γ-glutamylcysteine synthetase gene and provides a technique for producing a plant having an increased seed yield.

13 Claims, 20 Drawing Sheets

FIG. 1
(A)
Chl.*GSH1*
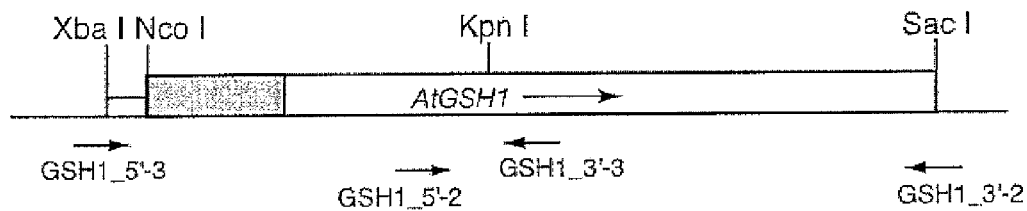
cyt.*GSH1*
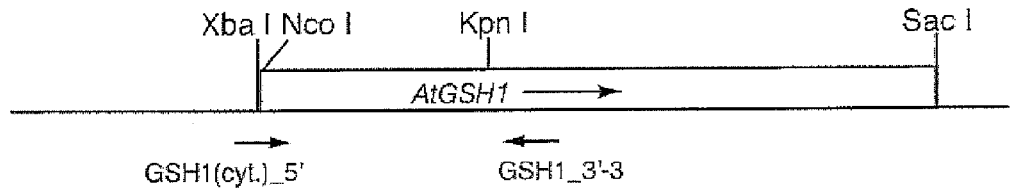
5'UTRcyt.*GSH1*
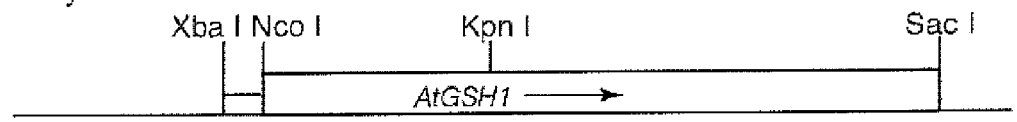
(B)
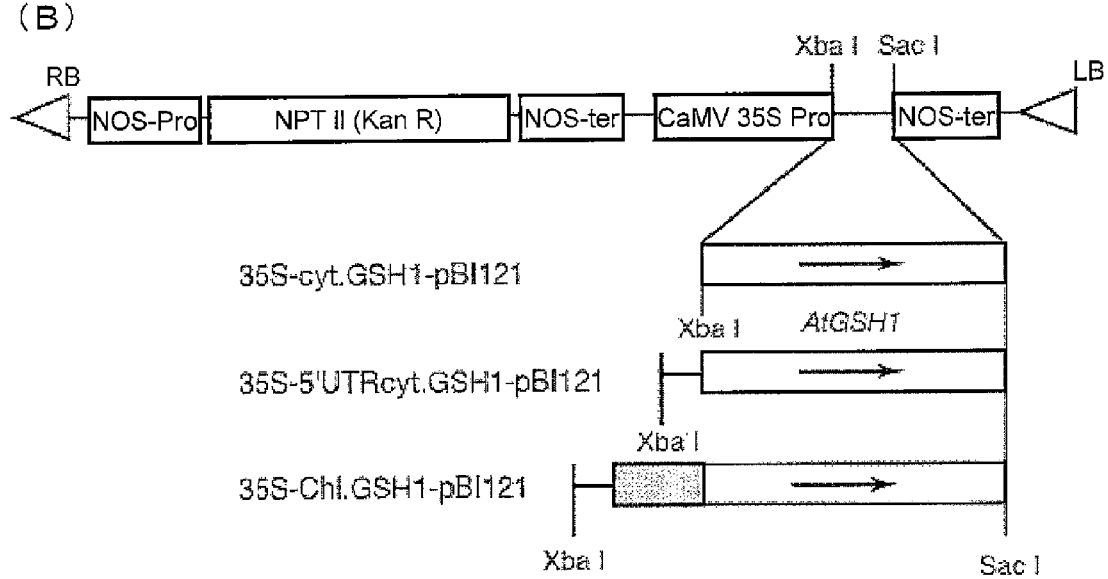

FIG. 13
(A)
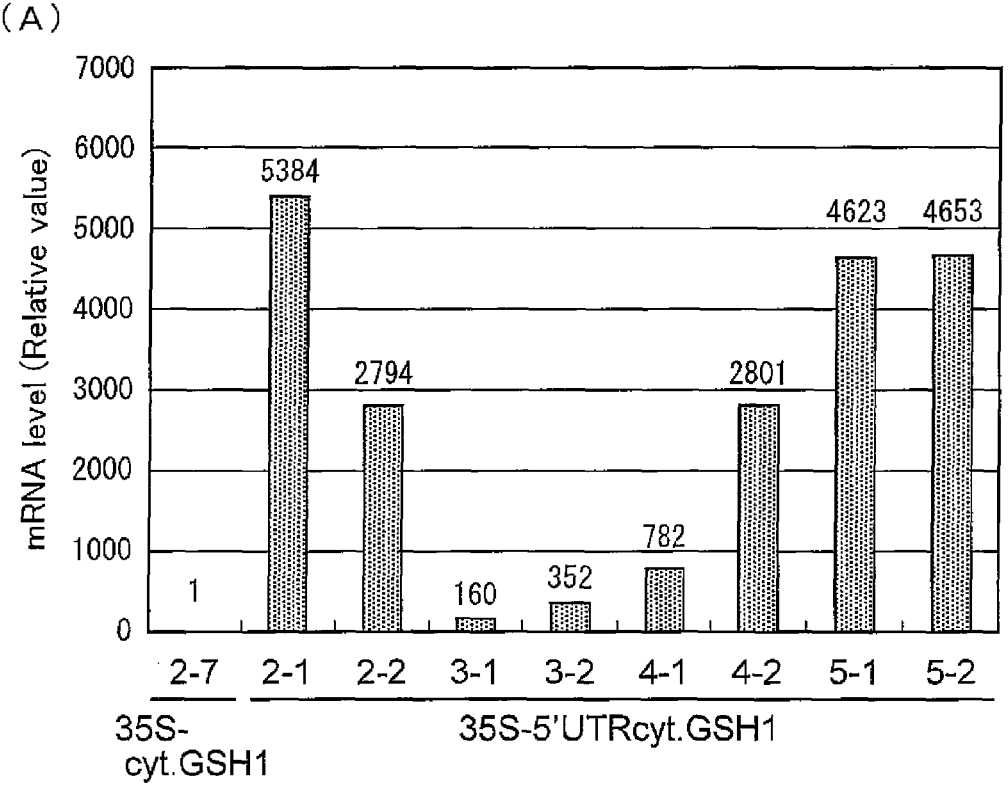
(B)
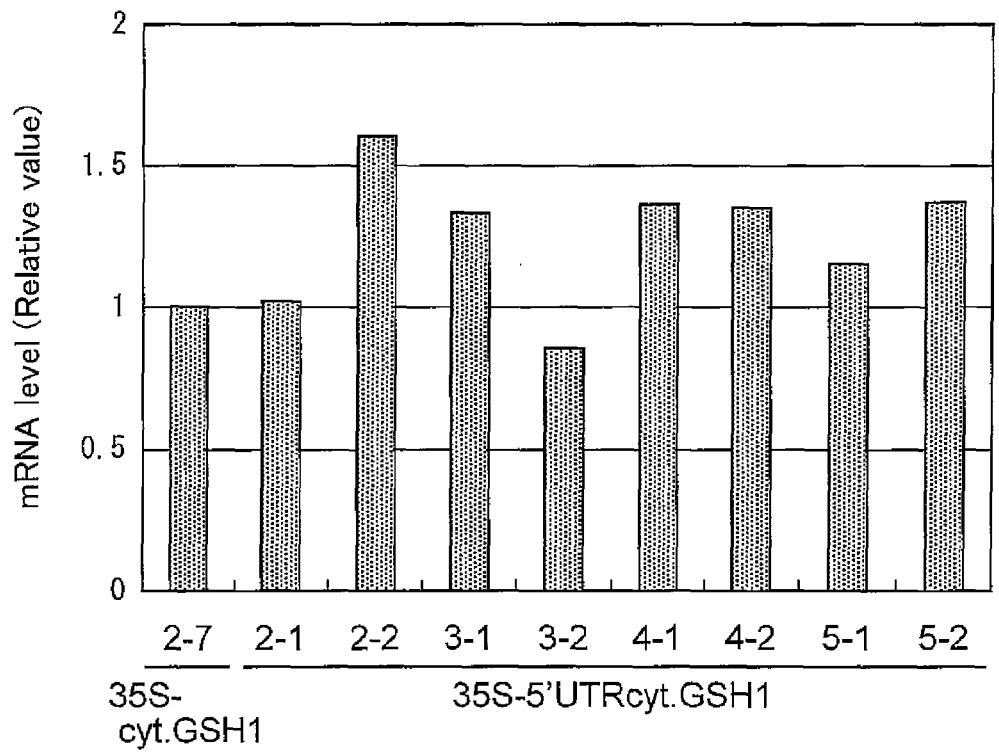

FIG. 14
(A)
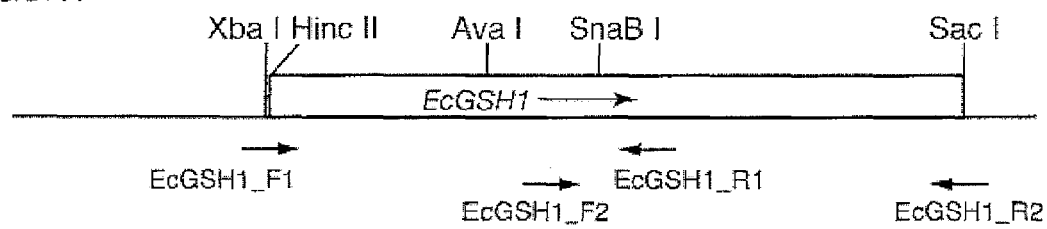
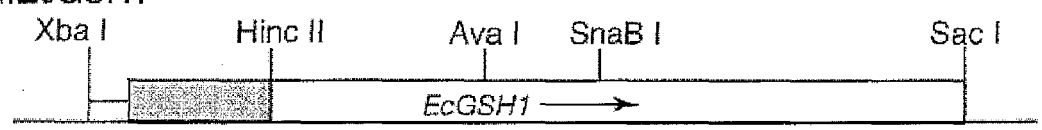
(B)
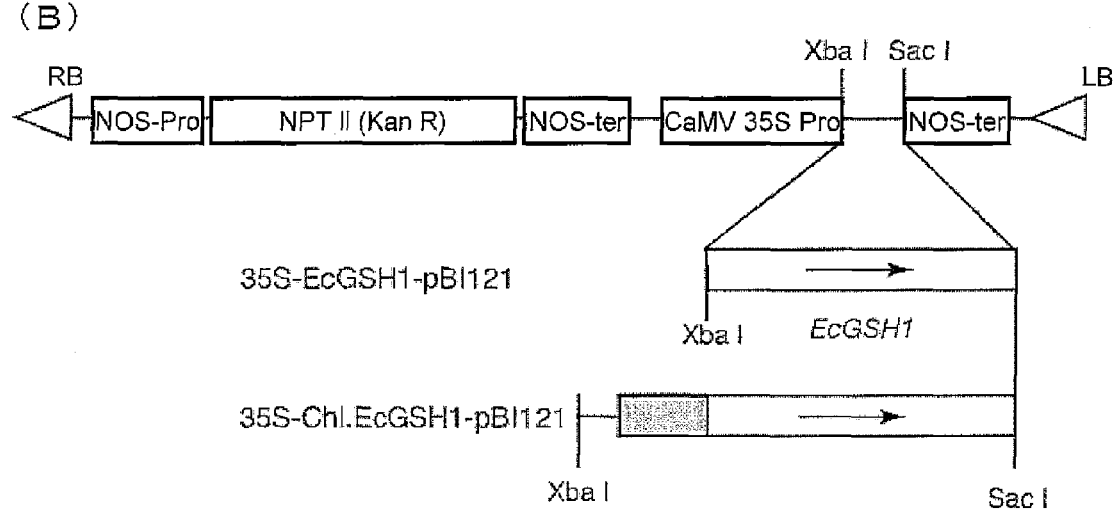

Col   35S-5'UTR cyt.GSH1

FIG. 18
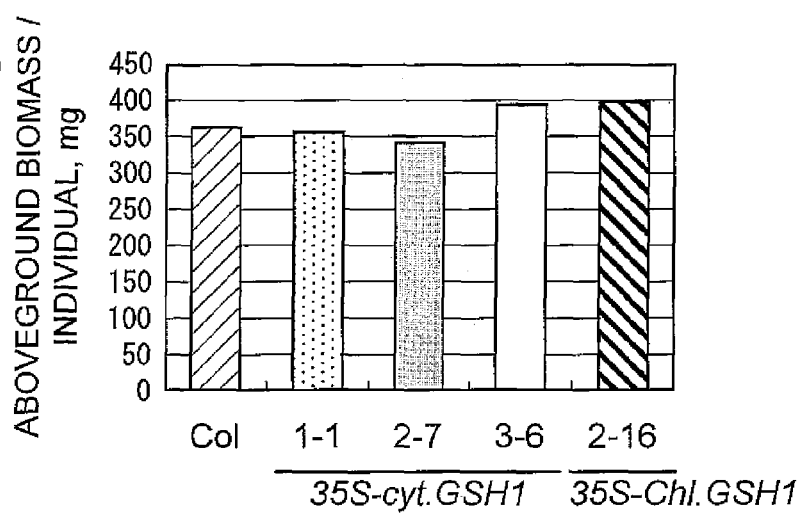
(A)
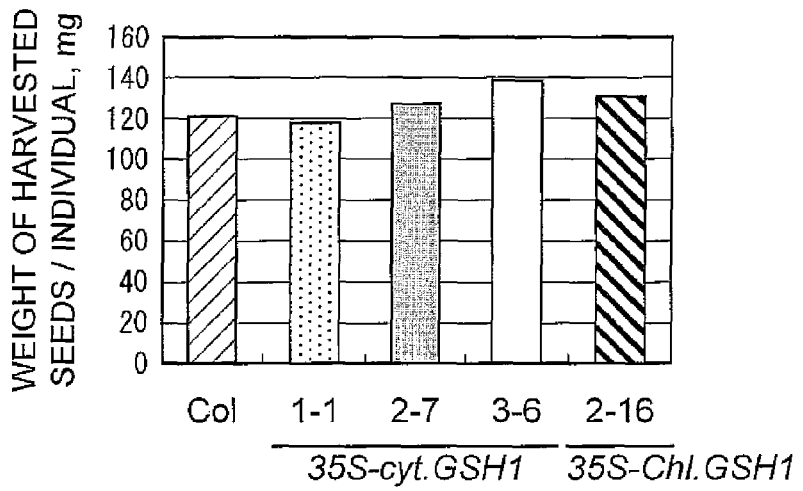
(B)
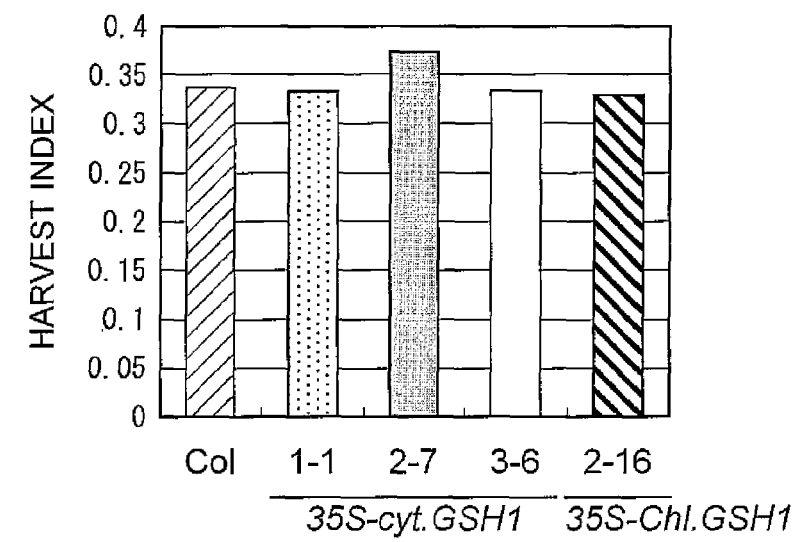
(C)

FIG. 19
(A)
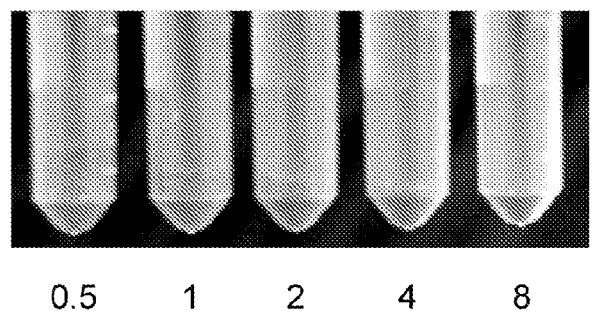
0.5　1　2　4　8
(B)
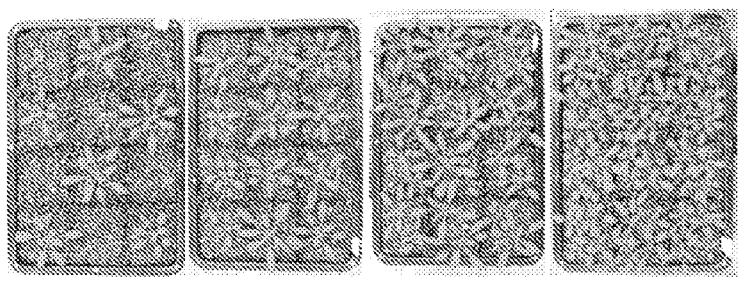
(C)
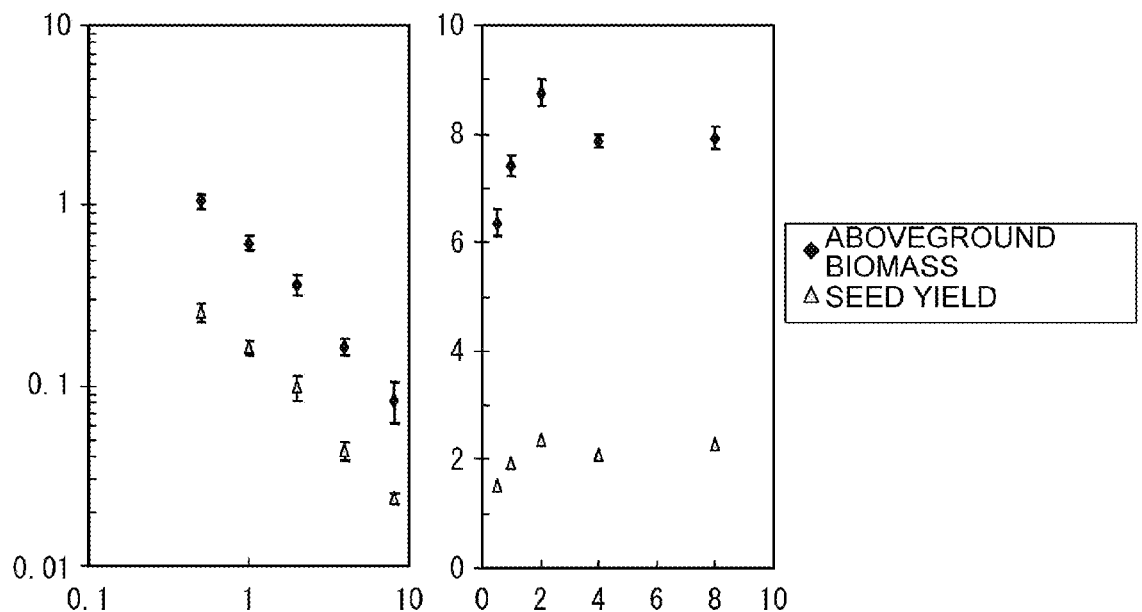
◆ ABOVEGROUND BIOMASS
△ SEED YIELD FIG. 20
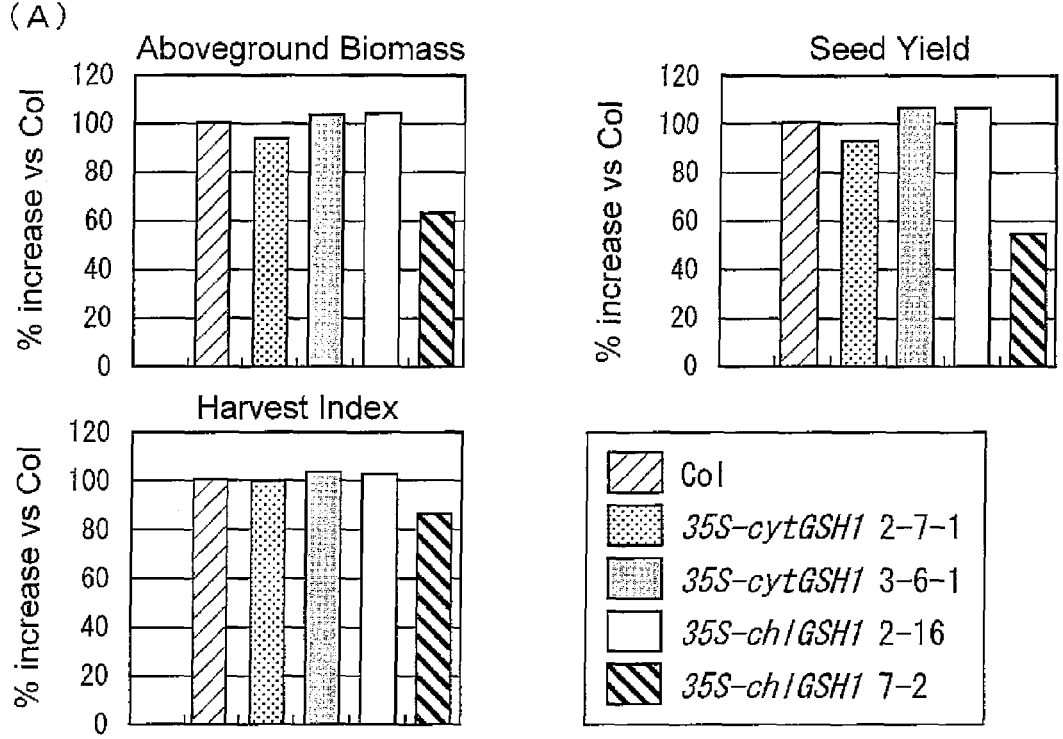
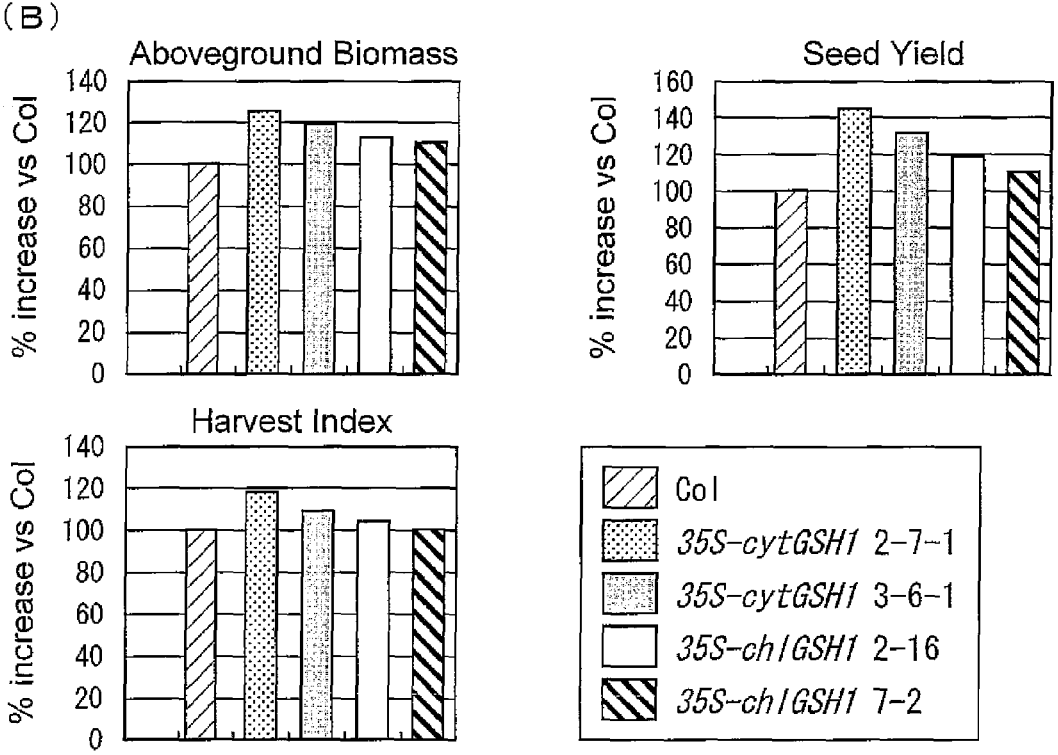

FIG. 25
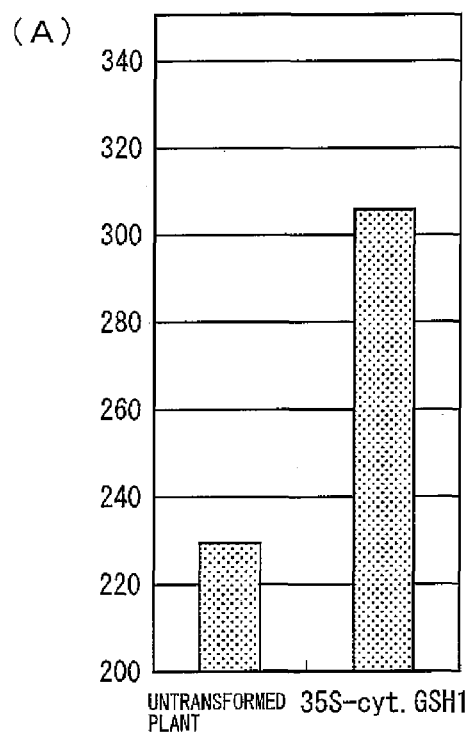
(A)
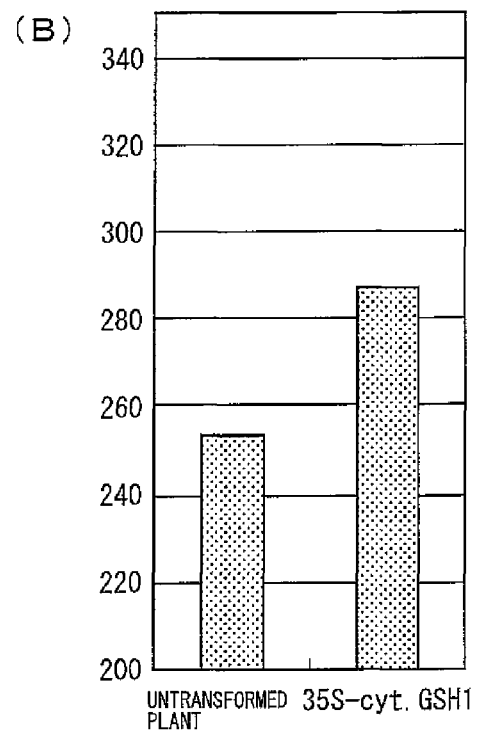
(B)
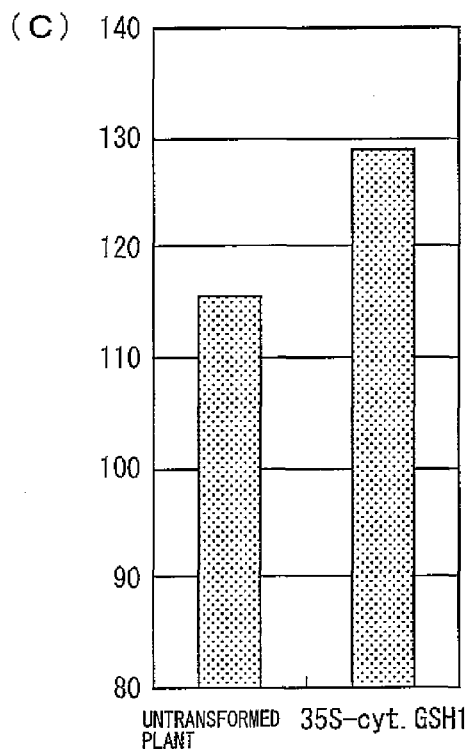
(C)
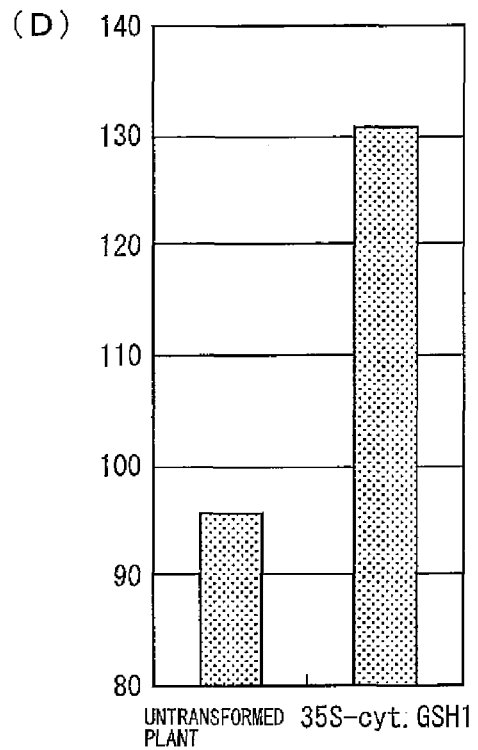
(D)

```
                              SEQUENCE LISTING

<160> NUMBER OF SEQ ID NOS: 28

<210> SEQ ID NO 1
<211> LENGTH: 522
<212> TYPE: PRT
<213> ORGANISM: Arabidopsis thaliana

<400> SEQUENCE: 1

Met Ala Leu Leu Ser Gln Ala Gly Gly Ser Tyr Thr Val Val Pro Ser
1               5                   10                  15

Gly Val Cys Ser Lys Ala Gly Thr Lys Ala Val Val Ser Gly Gly Val
            20                  25                  30

Arg Asn Leu Asp Val Leu Arg Met Lys Glu Ala Phe Gly Ser Ser Tyr
        35                  40                  45

Ser Arg Ser Leu Ser Thr Lys Ser Met Leu Leu His Ser Val Lys Arg
    50                  55                  60

Ser Lys Arg Gly His Gln Leu Ile Val Ala Ala Ser Pro Pro Thr Glu
65                  70                  75                  80

Glu Ala Val Val Ala Thr Glu Pro Leu Thr Arg Glu Asp Leu Ile Ala
                85                  90                  95

Tyr Leu Ala Ser Gly Cys Lys Thr Lys Asp Lys Tyr Arg Ile Gly Thr
            100                 105                 110

Glu His Glu Lys Phe Gly Phe Glu Val Asn Thr Leu Arg Pro Met Lys
        115                 120                 125

Tyr Asp Gln Ile Ala Glu Leu Leu Asn Gly Ile Ala Glu Arg Phe Glu
    130                 135                 140

Trp Glu Lys Val Met Glu Gly Asp Lys Ile Ile Gly Leu Lys Gln Gly
145                 150                 155                 160

Lys Gln Ser Ile Ser Leu Glu Pro Gly Gly Gln Phe Glu Leu Ser Gly
                165                 170                 175

Ala Pro Leu Glu Thr Leu His Gln Thr Cys Ala Glu Val Asn Ser His
            180                 185                 190

Leu Tyr Gln Val Lys Ala Val Ala Glu Glu Met Gly Ile Gly Phe Leu
        195                 200                 205

Gly Ile Gly Phe Gln Pro Lys Trp Arg Arg Glu Asp Ile Pro Ile Met
    210                 215                 220

Pro Lys Gly Arg Tyr Asp Ile Met Arg Asn Tyr Met Pro Lys Val Gly
225                 230                 235                 240

Thr Leu Gly Leu Asp Met Met Leu Arg Thr Cys Thr Val Gln Val Asn
                245                 250                 255

Leu Asp Phe Ser Ser Glu Ala Asp Met Ile Arg Lys Phe Arg Ala Gly
            260                 265                 270

Leu Ala Leu Gln Pro Ile Ala Thr Ala Leu Phe Ala Asn Ser Pro Phe
        275                 280                 285

Thr Glu Gly Lys Pro Asn Gly Phe Leu Ser Met Arg Ser His Ile Trp
    290                 295                 300

Thr Asp Thr Asp Lys Asp Arg Thr Gly Met Leu Pro Phe Val Phe Asp
305                 310                 315                 320

Asp Ser Phe Gly Phe Glu Gln Tyr Val Asp Tyr Ala Leu Asp Val Pro
                325                 330                 335
```

```
Met Tyr Phe Ala Tyr Arg Lys Asn Lys Tyr Ile Asp Cys Thr Gly Met
            340                 345                 350

Thr Phe Arg Gln Phe Leu Ala Gly Lys Leu Pro Cys Leu Pro Gly Glu
            355                 360                 365

Leu Pro Ser Tyr Asn Asp Trp Glu Asn His Leu Thr Thr Ile Phe Pro
            370                 375                 380

Glu Val Arg Leu Lys Arg Tyr Leu Glu Met Arg Gly Ala Asp Gly Gly
385                 390                 395                 400

Pro Trp Arg Arg Leu Cys Ala Leu Pro Ala Phe Trp Val Gly Leu Leu
                405                 410                 415

Tyr Asp Asp Ser Leu Gln Ala Ile Leu Asp Leu Thr Ala Asp Trp
                420                 425                 430

Thr Pro Ala Glu Arg Glu Met Leu Arg Asn Lys Val Pro Val Thr Gly
            435                 440                 445

Leu Lys Thr Pro Phe Arg Asp Gly Leu Leu Lys His Val Ala Glu Asp
450                 455                 460

Val Leu Lys Leu Ala Lys Asp Gly Leu Glu Arg Arg Gly Tyr Lys Glu
465                 470                 475                 480

Ala Gly Phe Leu Asn Ala Val Asp Glu Val Val Arg Thr Gly Val Thr
                485                 490                 495

Pro Ala Glu Lys Leu Leu Glu Met Tyr Asn Gly Glu Trp Gly Gln Ser
            500                 505                 510

Val Asp Pro Val Phe Glu Glu Leu Leu Tyr
            515                 520

<210> SEQ ID NO 2
<211> LENGTH: 1569
<212> TYPE: DNA
<213> ORGANISM: Arabidopsis thaliana

<400> SEQUENCE: 2
atggcgctct tgtctcaagc aggaggatca tacactgttg ttccttctgg agtttgttca      60
aaggctggaa ctaaagctgt tgtttcgggt ggcgtgagga atttggatgt tttgaggatg     120
aaagaagctt ttggtagctc ctactctagg agtctatcta ccaaatcaat gcttctccat     180
tctgttaaga ggagtaagag agggcatcaa ttgattgttg cggcaagtcc tccaacggaa     240
gaggctgtag ttgcaactga gccgttgacg agagaggatc tcattgccta tcttgcctct     300
ggatgcaaaa caaaggacaa atatagaata ggtacagaac atgagaaatt tggttttgag     360
gtcaatactt tgcgccctat gaagtatgat caaatagccg agcttcttaa tggtatcgct     420
gaaagatttg aatgggaaaa agtaatggaa ggtgacaaga tcattggtct gaagcaggga     480
aagcaaagca tttcacttga acctgggggt cagttcgagc ttagtggtgc acctcttgag     540
actttgcatc aaacttgtgc tgaagtcaat tcacatcttt atcaggtaaa agcagttgct     600
gaggaaatgg gaattggttt cttaggaatt ggcttccagc ccaaatggcg tcgggaggat     660
atacccatca tgccaaaggg gagatacgac attatgagaa actacatgcc gaaagttggt     720
acccttggtc ttgatatgat gctccgaacg tgtactgttc aggttaatct ggattttagc     780
tcagaagctg atatgatcag gaagtttcgt gctggtcttg ctttacaacc tatagcaacg     840
gctctatttg cgaattcccc ttttacagaa ggaaagccaa acggatttct cagcatgaga     900
agccacatat ggacagacac tgacaaggac cgcacaggaa tgctaccatt tgttttcgat     960
gactcttttg ggtttgagca gtatgttgac tacgcactcg atgtcccctat gtactttgcc    1020 tacagaaaga acaaatacat cgactgtact ggaatgacat tcggcaatt cttggctgga    1080
```

-continued

```
aaacttccct gtctccctgg tgaactgcct tcatataatg attgggaaaa ccatctgaca    1140
acaatattcc cagaggttcg gttgaagaga tacttggaga tgagaggtgc tgatggaggt    1200
ccctggagga ggctgtgtgc cctgccagct ttctgggtgg gtttattata tgatgatgat    1260
agtctccaag ctatcctgga tctgacagct gactggactc cagcagagag agagatgcta    1320
aggaacaaag tcccagttac tggcttaaag actccttttta gggatggttt gttaaagcat    1380
gtcgctgaag atgtcctgaa actcgcaaag gatggtttag agcgcagagg ctacaaggaa    1440
gccggtttct tgaacgcagt cgatgaagtg tcagaacag gagttacgcc tgcggagaag     1500
ctcttggaga tgtacaatgg agaatgggga caaagcgtag atcccgtgtt cgaagagctg    1560
ctgtactaa                                                            1569

<210> SEQ ID NO 3
<211> LENGTH: 449
<212> TYPE: PRT
<213> ORGANISM: Arabidopsis thaliana

<400> SEQUENCE: 3

Met Ala Ser Pro Pro Thr Glu Glu Ala Val Val Ala Thr Glu Pro Leu
1               5                   10                  15

Thr Arg Glu Asp Leu Ile Ala Tyr Leu Ala Ser Gly Cys Lys Thr Lys
            20                  25                  30

Asp Lys Tyr Arg Ile Gly Thr Glu His Glu Lys Phe Gly Phe Glu Val
        35                  40                  45

Asn Thr Leu Arg Pro Met Lys Tyr Asp Gln Ile Ala Glu Leu Leu Asn
    50                  55                  60

Gly Ile Ala Glu Arg Phe Glu Trp Glu Lys Val Met Glu Gly Asp Lys
65                  70                  75                  80

Ile Ile Gly Leu Lys Gln Gly Lys Gln Ser Ile Ser Leu Glu Pro Gly
                85                  90                  95

Gly Gln Phe Glu Leu Ser Gly Ala Pro Leu Glu Thr Leu His Gln Thr
            100                 105                 110

Cys Ala Glu Val Asn Ser His Leu Tyr Gln Val Lys Ala Val Ala Glu
        115                 120                 125

Glu Met Gly Ile Gly Phe Leu Gly Ile Gly Phe Gln Pro Lys Trp Arg
    130                 135                 140

Arg Glu Asp Ile Pro Ile Met Pro Lys Gly Arg Tyr Asp Ile Met Arg
145                 150                 155                 160

Asn Tyr Met Pro Lys Val Gly Thr Leu Gly Leu Asp Met Met Leu Arg
                165                 170                 175

Thr Cys Thr Val Gln Val Asn Leu Asp Phe Ser Ser Glu Ala Asp Met
            180                 185                 190

Ile Arg Lys Phe Arg Ala Gly Leu Ala Leu Gln Pro Ile Ala Thr Ala
        195                 200                 205

Leu Phe Ala Asn Ser Pro Phe Thr Glu Gly Lys Pro Asn Gly Phe Leu
    210                 215                 220

Ser Met Arg Ser His Ile Trp Thr Asp Thr Asp Lys Asp Arg Thr Gly
225                 230                 235                 240

Met Leu Pro Phe Val Phe Asp Asp Ser Phe Gly Phe Glu Gln Tyr Val
                245                 250                 255

Asp Tyr Ala Leu Asp Val Pro Met Tyr Phe Ala Tyr Arg Lys Asn Lys
            260                 265                 270

Tyr Ile Asp Cys Thr Gly Met Thr Phe Arg Gln Phe Leu Ala Gly Lys
        275                 280                 285
```

```
Leu Pro Cys Leu Pro Gly Glu Leu Pro Ser Tyr Asn Asp Trp Glu Asn
        290                 295                 300

His Leu Thr Thr Ile Phe Pro Glu Val Arg Leu Lys Arg Tyr Leu Glu
305                 310                 315                 320

Met Arg Gly Ala Asp Gly Gly Pro Trp Arg Arg Leu Cys Ala Leu Pro
                325                 330                 335

Ala Phe Trp Val Gly Leu Leu Tyr Asp Asp Asp Ser Leu Gln Ala Ile
                340                 345                 350

Leu Asp Leu Thr Ala Asp Trp Thr Pro Ala Glu Arg Glu Met Leu Arg
            355                 360                 365

Asn Lys Val Pro Val Thr Gly Leu Lys Thr Pro Phe Arg Asp Gly Leu
        370                 375                 380

Leu Lys His Val Ala Glu Asp Val Leu Lys Leu Ala Lys Asp Gly Leu
385                 390                 395                 400

Glu Arg Arg Gly Tyr Lys Glu Ala Gly Phe Leu Asn Ala Val Asp Glu
                405                 410                 415

Val Val Arg Thr Gly Val Thr Pro Ala Glu Lys Leu Leu Glu Met Tyr
            420                 425                 430

Asn Gly Glu Trp Gly Gln Ser Val Asp Pro Val Phe Glu Leu Leu
        435                 440                 445

Tyr

<210> SEQ ID NO 4
<211> LENGTH: 1350
<212> TYPE: DNA
<213> ORGANISM: Arabidopsis thaliana

<400> SEQUENCE: 4
atggcaagtc ctccaacgga agaggctgta gttgcaactg agccgttgac gagagaggat      60
ctcattgcct atcttgcctc tggatgcaaa acaaaggaca atatagaat aggtacagaa      120 catgagaaat ttggttttga ggtcaatact ttgcgcccta tgaagtatga tcaaatagcc     180
gagcttctta atggtatcgc tgaaagattt gaatgggaaa agtaatgga aggtgacaag      240 atcattggtc tgaagcaggg aaagcaaagc atttcacttg aacctggggg tcagttcgag     300
cttagtggtg cacctcttga ctttgcat caaacttgtg ctgaagtcaa ttcacatctt       360
tatcaggtaa aagcagttgc tgaggaaatg ggaattggtt tcttaggaat tggcttccag      420
cccaaatggc gtcggaagga atacccatc atgccaaagg ggagatacga cattatgaga      480
aactacatgc cgaaagttgg taccettggt cttgatatga tgctccgaac gtgtactgtt     540
caggttaatc tggattttag ctcagaagct gatatgatca ggaagttttcg tgctggtctt    600 gctttacaac ctatagcaac ggctctattt gcgaattccc ctttttacaga aggaaagcca    660 aacggatttc tcagcatgag aagccacata tggacagaca ctgacaagga ccgcacagga     720
atgctaccat ttgttttcga tgactctttt gggtttgagc agtatgttga ctacgcactc    780
gatgtcccta tgtactttgc ctacagaaag aacaaataca tcgactgtac tggaatgaca    840
tttcggcaat tcttggctgg aaaacttccc tgtctccctg gtgaactgcc ttcatataat    900
gattgggaaa accatctgac aacaatattc ccagaggttc ggttgaagag atacttggag    960
atgagaggtg ctgatggagg tccctggagg aggctgtgtg ccctgccagc tttctgggtg    1020
ggtttattat atgatgatga tagtctccaa gctatcctgg atctgacagc tgactggact    1080
ccagcagaga gagagatgct aaggaacaaa gtcccagtta ctggcttaaa gactcctttt    1140
agggatggtt tgttaaagca tgtcgctgaa gatgtcctga aactcgcaaa ggatggttta    1200
```

| | |
|---|---|
| gagcgcagag gctacaagga agccggtttc ttgaacgcag tcgatgaagt ggtcagaaca | 1260 |
| ggagttacgc ctgcggagaa gctcttggag atgtacaatg gagaatgggg acaaagcgta | 1320 |
| gatcccgtgt tcgaagagct gctgtactaa | 1350 |

<210> SEQ ID NO 5
<211> LENGTH: 2036
<212> TYPE: DNA
<213> ORGANISM: Arabidopsis thaliana

<400> SEQUENCE: 5

| | |
|---|---|
| atgctccact gatcaacttt ctttcatttt tttatcagtt tctcatttct ctctcagtcg | 60 |
| catataaatt tgaaacgccg attcgttttt gctctttaag ctttcttctt gatttcgacg | 120 |
| gtgtctctca atctccgtca agcttgacga atttcaggag ctatatatac catggcgctc | 180 |
| ttgtctcaag caggaggatc atacactgtt gttccttctg gagtttgttc aaaggctgga | 240 |
| actaaagctg ttgtttcggg tggcgtgagg aatttggatg ttttgaggat gaaagaagct | 300 |
| tttggtagct cctactctag gagtctatct accaaatcaa tgcttctcca ttctgttaag | 360 |
| aggagtaaga gagggcatca attgattgtt gcggcaagtc ctccaacgga agaggctgta | 420 |
| gttgcaactg agccgttgac gagagaggat ctcattgcct atcttgcctc tggatgcaaa | 480 |
| acaaaggaca atatagaat aggtacgaaa catgagaaat tggttttga ggtcaatact | 540 |
| ttgcgcccta tgaagtatga tcaaatagcc gagcttctta atggtatcgc tgaaagattt | 600 |
| gaatgggaaa agtaatgga aggtgacaag atcattggtc tgaagcaggg aaagcaaagc | 660 |
| atttcacttg aacctggggg tcagttcgag cttagtggtg cacctcttga ctttgcat | 720 |
| caaacttgtg ctgaagtcaa ttcacatctt tatcaggtaa aagcagttgc tgaggaaatg | 780 |
| ggaattggtt tcttaggaat tggcttccag cccaaatggc gtcgggagga tatacccatc | 840 |
| atgccaaagg ggagatacga cattatgaga aactacatgc cgaaagttgg taccctggt | 900 |
| cttgatatga tgctccgaac gtgtactgtt caggttaatc tggattttag ctcagaagct | 960 |
| gatatgatca ggaagtttcg tgctggtctt gctttacaac ctatagcaac ggctctattt | 1020 |
| gcgaattccc cttttacaga aggaaagcca aacggatttc tcagcatgag aagccacata | 1080 |
| tggacagaca ctgacaagga ccgcacagga atgctaccat tgttttcga tgactctttt | 1140 |
| gggtttgagc agtatgttga ctacgcactc gatgtcccta tgtactttgc ctacagaaag | 1200 |
| aacaaataca tcgactgtac tggaatgaca tttcggcaat tcttggctgg aaaacttccc | 1260 |
| tgtctccctg gtgaactgcc ttcatataat gattgggaaa accatctgac aacaatattc | 1320 |
| ccagaggttc ggttgaagag atacttggag atgagaggtg ctgatggagg tccctggagg | 1380 |
| aggctgtgtg ccctgccagc tttctgggtg ggtttattat atgatgatga tagtctccaa | 1440 |
| gctatcctgg atctgacagc tgactggact ccagcagaga gagatgct aaggaacaaa | 1500 |
| gtcccagtta ctggcttaaa gactccttt agggatggtt tgttaaagca tgtcgctgaa | 1560 |
| gatgtcctga aactcgcaaa ggatggttta gagcgcagag gctacaagga agccggtttc | 1620 |
| ttgaacgcag tcgatgaagt ggtcagaaca ggagttacgc ctgcggagaa gctcttggag | 1680 |
| atgtacaatg gagaatgggg acaaagcgta gatcccgtgt tcgaagagct gctgtactaa | 1740 |
| gaaaatggga cgtgaacaaa aggtgtctat aaacctttgg gtgtgagttt atgctatctg | 1800 |
| aagaattcga gtctccggaa taaggatttt tttttttgtt gtaatcggat tttaaaaact | 1860 |
| gattttgttt tagaaattcg aagcattgaa aagcagaaga aaaattgtat gtactaaacg | 1920 |
| atttcggtgt gggaaatcgt ttgggagggt gtgtttggat cttgaataaa ttacccattt | 1980 |

```
ttcttgtcac aaatttgtct acatttaacg aaataactca aaactgattt caaggc        2036
```

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6

```
gctttcttct agatttcgac gg                                              22
```

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7

```
cctgatcata tcagcttctg agc                                             23
```

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8

```
atgccaaagg ggagatacga                                                 20
```

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9

```
ggagactcga gctcttcaga tag                                             23
```

<210> SEQ ID NO 10
<211> LENGTH: 27
<212> TYPE: DNA
<213> ORGANISM: Artificial
<220> FEATURE:
<223> OTHER INFORMATION: Primer

<400> SEQUENCE: 10

```
agggcatcta gagaccatgg caagtcc                                         27
```

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11

```
cttgatatga tgctccgaac                                                 20
```

<210> SEQ ID NO 12
<211> LENGTH: 24
<212> TYPE: DNA
<213> ORGANISM: Artificial

```
<220> FEATURE:
<223> OTHER INFORMATION: Primer

<400> SEQUENCE: 12
atcatataat aaacccaccc agaa                                          24

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
gatgatgcac ctagagctgt                                               20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ctccatgtca tcccaattgt                                               20

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
aattgattgc cgcggcaagt cc                                            22

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
ctatatatac cgcggcgctc ttgtc                                         25

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
ccagaggcaa gataggcaat g                                             21

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
cctcacgcca cccgaaacaa                                               20
```

```
<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19
tgcggagaag ctcttggaga tg                                              22

<210> SEQ ID NO 20
<211> LENGTH: 22
<212> TYPE: DNA
<213> ORGANISM: Artificial
<220> FEATURE:
<223> OTHER INFORMATION: Primer

<400> SEQUENCE: 20
ccgtgttcga agagctgctg ta                                              22

<210> SEQ ID NO 21
<211> LENGTH: 23
<212> TYPE: DNA
<213> ORGANISM: Artificial
<220> FEATURE:
<223> OTHER INFORMATION: Primer

<400> SEQUENCE: 21
ttccggagac tcgaattctt cag                                             23

<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
ccaaatgttt gaacgatcgg gg                                              22

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
tcctagtaag cgcgagtcat c                                               21

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cgaacacttc accggatcat                                                 20

<210> SEQ ID NO 25
<211> LENGTH: 30
<212> TYPE: DNA
<213> ORGANISM: Artificial
<220> FEATURE:
<223> OTHER INFORMATION: Primer

<400> SEQUENCE: 25
```

```
tttgacagtc tagagttgac tatgatcccg                                    30

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
ttccgatggc gttttgattg cc                                            22

<210> SEQ ID NO 27
<211> LENGTH: 25
<212> TYPE: DNA
<213> ORGANISM: Artificial
<220> FEATURE:
<223> OTHER INFORMATION: Primer

<400> SEQUENCE: 27
tcgtttgagc gatctcggct atacc                                         25

<210> SEQ ID NO 28
<211> LENGTH: 24
<212> TYPE: DNA
<213> ORGANISM: Artificial
<220> FEATURE:
<223> OTHER INFORMATION: Primer

<400> SEQUENCE: 28
aattttggga gctcacgagt ggcc                                          24
```

PLANT HAVING INCREASED YIELD OF SEEDS

CROSS-REFERENCE TO RELATED APPLICATIONS

This application is the national stage application pursuant to 35 U.S.C. §371 of PCT International Application No. PCT/JP2008/050341, filed Jan. 15, 2008, which claims priority to Japanese patent application no. 2007/7464, filed Jan. 16, 2007. The contents of these applications are incorporated herein by reference in their entirety.

TECHNICAL FIELD

The present invention relates to plants having an increased seed yield. More specifically, the present invention relates to (i) plants in which at least one of the number of flowers, the number of seeds, and the weight of seeds is increased by introducing a plant-derived γ-glutamylcysteine sysnthetase gene into the plant and (ii) a method for increasing at least one of the number of flowers and the number of seeds of a plant.

BACKGROUND ART

Conventionally, plants have been deeply involved with human as foods, ornaments, industrial materials such as paper and chemicals, and fuels. Further, recently, plants have been spotlighted as biomass energy that will substitute fossil fuel.

Although plants have been used in such various fields, their mechanisms such as germination, growth, and flowering have not yet been clarified in many regards. Consequently, cultivation of plants has been mainly based on experiences and intuition, and harvest of the plants has been greatly influenced by natural conditions such as weather. Therefore, clarification of plants' mechanisms such as germination, growth, and flowering and regulating and controlling the mechanisms are very important not only for increasing yields of ornamental plants and food plants such as cereals and vegetables, but also for growing woods in forests and biomass energy.

In order to regulate growth of plants, there have been made attempts such as regulation of flowering by artificial environments such as a conservatory, and promotion of growth by use of chemicals such as ethylene. However, most of these conventional attempts are regulations of growth of plants based on experiences and intuition, and are not based on data that allows scientific evaluation of growth of plants.

The inventors of the present invention have researched on the plant's mechanisms of germination, growth, and flowering. Consequently, the inventors have shown that a redox status adjusting substance such as reactive oxygen and glutathione is essential as a factor for controlling growth of plants (see Patent Literatures 1 and 2).

Glutathione (GSH) is a tripeptide that is synthesized in such a manner that γ-glutamylcysteine is synthesized from cysteine and glutamic acid by γ-glutamylcysteine synthetase and glycine is then added to γ-glutamylcysteine by GSH synthetase. Glutathione is a main intracellular antioxidant, and has a function of detoxifying a foreign matter in the cell.

It has been reported that a transformed plant to which a γ-glutamylcysteine synthetase gene of Escherichia coli is introduced is efficiently increased in glutathione content (see Non Patent Literatures 1 to 3). However, it has been also reported that such a transformed plant may become intolerant to light (see Non Patent Literature 3).

On the other hand, it has been reported that in a case where γ-glutamylcysteine synthetase gene of the plant itself is overexpressed, i.e., in a case of a transformed plant in which γ-glutamylcysteine synthetase gene of Arabidopsis thaliana is introduced into Arabidopsis thaliana and then overexpressed, the expression levels of γ-glutamylcysteine synthetase mRNA and translated product thereof (protein) are greatly increased, whereas the glutathione content is not so much increased (see Non Patent Literature 4). Therefore, it has been recognized that use of a plant-derived γ-glutamylcysteine synthetase gene is not a good method for increasing the glutathione content in the plant.

CITATION LIST

Patent Literature 1
International Publication No. WO01/080638 (Publication Date: Jul. 22, 2003)
Patent Literature 2
Japanese Patent Application Publication, Tokukai, No. 2004-352679 A (Publication Date: Dec. 16, 2004)
Non Patent Literature 1
Noctor G, Strohm M, Jouanin L, Kunert K J, Foyer C H, Rennenberg H. Synthesis of glutathione in leaves of transgenic poplar overexpressing γ-glutamylcysteine synthetase. Plant Physiol. 1996 November; 112(3):1071-1078.
Non Patent Literature 2
Noctor G, Arisi A C, Jouanin L, Foyer C H. Manipulation of glutathione and amino acid biosynthesis in the chloroplast. Plant Physiol. 1998 October; 118(2):471-482.
Non Patent Literature 3
Creissen G, Firmin J, Fryer M, Kular B, Leyland N, Reynolds H, Pastori G, Wellburn F, Baker N, Wellburn A, Mullineaux P. Elevated glutathione biosynthetic capacity in the chloroplasts of transgenic tobacco plants paradoxically causes increased oxidative stress. Plant Cell. 1999 July; 11(7):1277-1292.
Non Patent Literature 4
Xiang C, Werner B L, Christensen E M, Oliver D J. The biological functions of glutathione revisited in arabidopsis transgenic plants with altered glutathione levels. Plant Physiol. 2001 June; 126(2):564-574.

SUMMARY OF INVENTION

As described above, attempts have been made to increase glutathione content in a plant by introducing γ-glutamylcysteine synthetase gene into the plant (see Non Patent Literatures 1 to 4). In this regard, although it has been reported that introduction of the γ-glutamylcysteine synthetase gene into the plant (see Non Patent Literature 4) does not have a great influence on a normal growth process (morphology or the like) of the plant under nonstressed condition, it has not been analyzed in terms of an influence on yields.

Further, since it is considered to be difficult to greatly increase the glutathione content even by introducing a plant-derived γ-glutamylcysteine synthetase gene into a plant, groups other than the group of the present inventors have studies little on how a plant-derived γ-glutamylcysteine synthetase gene product affects growth of plants.

However, since the inventors of the present invention had found that glutathione is effective as a growth regulator of a plant, the inventors assumed that an endogenous glutathione synthesis system should be affected in any way as a plant grows. Scientifically understanding the process of growth of plants, scientifically predicting flowering time, and regulating them are very important not only to ornamental flowers and plants for foods, but also to forests and plant resources for biomass energy. Therefore, it is of great significance to elucidate the function of the gene product of the plant-derived γ-glutamylcysteine synthetase which catalyzes the first step of the synthesis system and thereby clarify the relationship between the gene product and the growth of plants in the aim of clarifying an unknown control system of the endogenous glutathione synthesis.

As a result of the study, the inventors of the present invention found that the control of the glutathione synthesis is closely related to seed yields, and that the control is attributed to the γ-glutamylcysteine synthetase gene product which catalyzes the first step of the synthesis.

An object of the present invention is to provide, based on the finding, a technique for producing a plant having an increased seed yield.

In the course of studying a control mechanism of the plant-derived γ-glutamylcysteine synthetase gene product in the growth of plants, the inventors of the present invention found that plants in which an expression level of the γ-glutamylcysteine synthetase gene was increased, among those to which the plant-derived γ-glutamylcysteine synthetase gene was introduced, showed an increase in the number of flowers and seeds in comparison with its parent plant under a cultivation condition where the planting density was higher than that which allows sufficient increases in biomass quantity per unit area and in seed yield per unit area. Based on this finding, the inventors of the present invention accomplished the present invention.

That is, a plant according to the present invention has a mutation that causes an increase in a level of γ-glutamylcysteine synthetase activity, the plant being further increased in biomass quantity per unit area or seed yield per unit area in comparison with a parent plant thereof by being cultivated at a planting density higher than that which allows sufficient increases in the biomass quantity per unit area and in the seed yield per unit area.

Further, the plant according to the present invention has a mutation that causes an increase in an expression level of γ-glutamylcysteine synthetase, the plant being further increased in biomass quantity per unit area or seed yield per unit area in comparison with a wild-type plant by being cultivated at a planting density higher than that which allows sufficient increases in the biomass quantity per unit area and in the seed yield per unit area.

Furthermore, the transformed plant according to the present invention into which a polynucleotide encoding plant-derived γ-glutamylcysteine synthetase is introduced, the plant being further increased in biomass quantity per unit area or seed yield per unit area in comparison with a parent plant thereof by being cultivated at a planting density higher than that which allows sufficient increases in the biomass quantity per unit area and in the seed yield per unit area.

In the transformed plant according to the present invention, it is preferable that a translated product of the polynucleotide encoding the plant-derived γ-glutamylcysteine synthetase has a chloroplast targeting signal peptide.

The polynucleotide encoding the γ-glutamylcysteine synthetase having the chloroplast targeting signal peptide is preferably selected from the group consisting of the following (a) to (d):

(a) a polynucleotide encoding a polypeptide having the amino-acid sequence represented by SEQ ID NO: 1;

(b) a polynucleotide encoding a polypeptide having an amino-acid sequence in which one or several amino acids of which are deleted, substituted, or added from/in/to the amino-acid sequence represented by SEQ ID NO: 1;

(c) a polynucleotide having the base sequence represented by SEQ ID NO: 2; and (d) a polynucleotide that hybridizes, under a stringent condition, with the polynucleotide having the base sequence represented by SEQ ID NO: 2;

In the transformed plant according to the present invention, it is preferable that a translated product of the polynucleotide encoding the plant-derived γ-glutamylcysteine synthetase does not have a chloroplast targeting signal peptide, and has an improved harvest index.

The polynucleotide encoding γ-glutamylcysteine synthetase having no chloroplast targeting signal peptide is selected from the group consisting of the following (e) to (h):

(e) a polynucleotide encoding a polypeptide having the amino-acid sequence represented by SEQ ID NO: 3;

(f) a polynucleotide encoding a polypeptide having an amino-acid sequence in which one or several amino acids of which are deleted, substituted, or added from/in/to the amino-acid sequence represented by SEQ ID NO: 3;

(g) a polynucleotide having the base sequence represented by SEQ ID NO: 4; and (h) a polynucleotide that hybridizes, under a stringent condition, with the polynucleotide having the base sequence represented by SEQ ID NO: 4.

The transformed plant according to the present invention may be such that a polynucleotide encoding glutathione-binding aldolase is further introduced thereinto.

A method according to the present invention is a method for increasing at least one of the number of flowers of a plant and the number of seeds of the plant, the method including the steps of: introducing, into the plant, polynucleotide encoding γ-glutamylcysteine synthetase; and cultivating the plant, into which the polynucleotide is introduced, at a planting density higher than that which allows sufficient increases in biomass quantity per unit area and in seed yield per unit area.

In the method of the present invention, it is preferable that the polynucleotide encoding the γ-glutamylcysteine synthetase be selected from the group consisting of the following (a) to (h):

(a) a polynucleotide encoding a polypeptide having the amino-acid sequence represented by SEQ ID NO: 1;

(b) a polynucleotide encoding a polypeptide having an amino-acid sequence in which one or several amino acids of which are deleted, substituted, or added from/in/to the amino-acid sequence represented by SEQ ID NO: 1;

(c) a polynucleotide having the base sequence represented by SEQ ID NO: 2; and (d) a polynucleotide that hybridizes, under a stringent condition, with the polynucleotide having the base sequence represented by SEQ ID NO: 2.

(e) a polynucleotide encoding a polypeptide having the amino-acid sequence represented by SEQ ID NO: 3;

(f) a polynucleotide encoding a polypeptide having an amino-acid sequence in which one or several amino acids of which are deleted, substituted, or added from/in/to the amino-acid sequence represented by SEQ ID NO: 3;

(g) a polynucleotide having the base sequence represented by SEQ ID NO: 4; and (h) a polynucleotide that hybridizes, under a stringent condition, with the polynucleotide having the base sequence represented by SEQ ID NO: 4.

For a fuller understanding of the nature and advantages of the invention, reference should be made to the ensuing detailed description taken in conjunction with the accompanying drawings.

BRIEF DESCRIPTION OF DRAWINGS

A of FIG. 1 illustrates primers and restriction enzyme recognition sites that were used in cloning a GSH1 gene having a chloroplast targeting signal peptide and a GSH1 gene having no chloroplast targeting signal peptide. B of FIG. 1 illustrates constructs that were used in transformation.

FIG. 10 is a graph showing an endogenous glutathione level in a transformed plant into which 35S-cyt.GSH1-pBI121 was introduced.

A of FIG. 13 is a graph showing the results of quantitative RT-PCR performed on GSH1 mRNAs derived from 35S-GSH1-pBI121 (35S-cyt.GSH1-pBI121 or 35S-5'UTR-cyt.GSH1-pBI121), the GSH1 mRNAs being obtained from a transformed plant (35S-cyt.GSH1 (2-7)) into which the 35S-cyt.GSH1-pBI121 was introduced and a transformed plant into which the 35S-5'UTRcyt.GSH1-pBI121 was introduced. B of FIG. 13 is a graph showing the results of quantitative RT-PCR performed on GSH1 mRNAs derived from a host genome, the GSH1 mRNAs being obtained from the same plants as in A of FIG. 13. The results are indicated as a relative value, with a level of GSH1 mRNA of 35S-cyt.GSH1 (2-7) being 1.

A of FIG. 14 illustrates primers and restriction enzyme recognition sites that were used in cloning an *Escherichia coli*-derived GSH1 gene. B of FIG. 14 illustrates constructs that were used in transformation.

Figure 15:
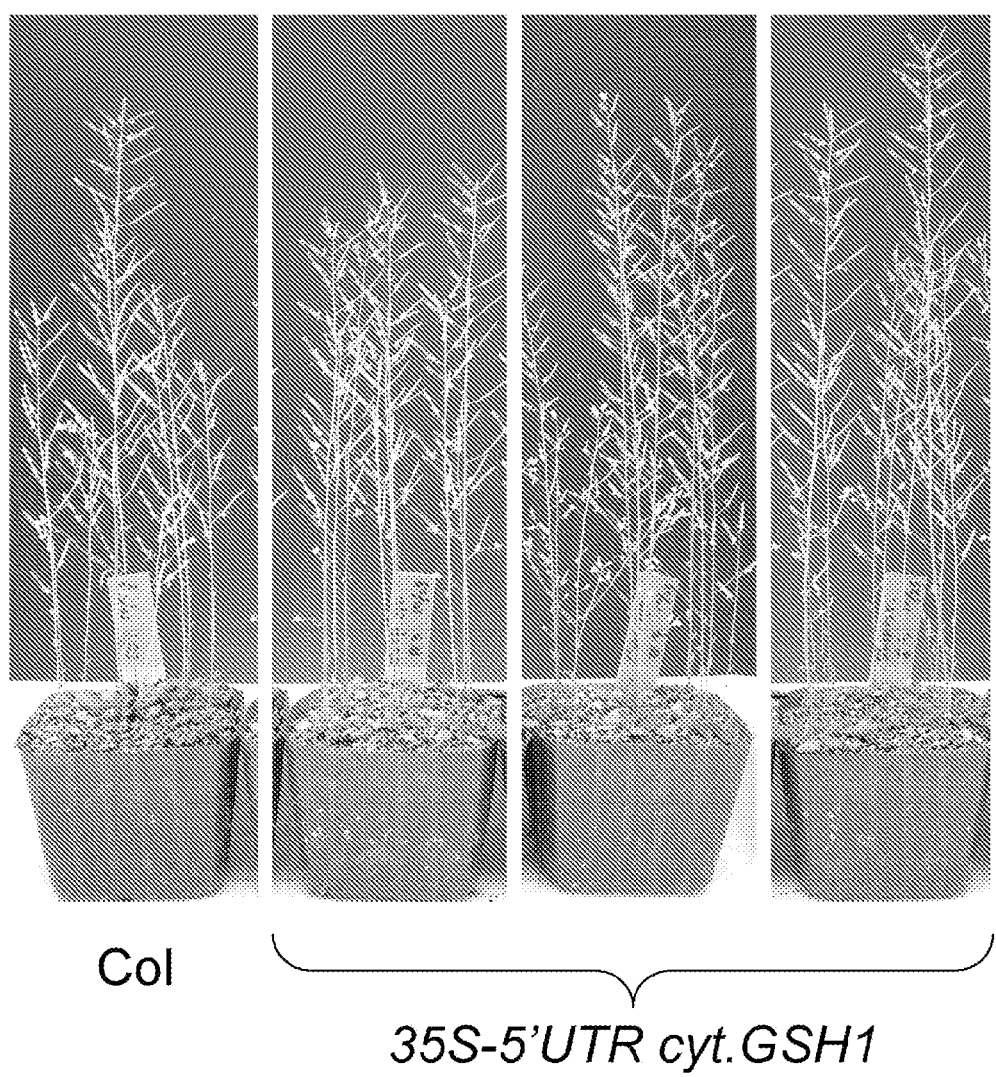

FIG. 15 shows photographs indicating that plants in which stability of mRNA was increased by inserting a 5'-untranslated region of a GSH1 gene was improved in growth efficiency and productivity in comparison with Col.

Figure 16:
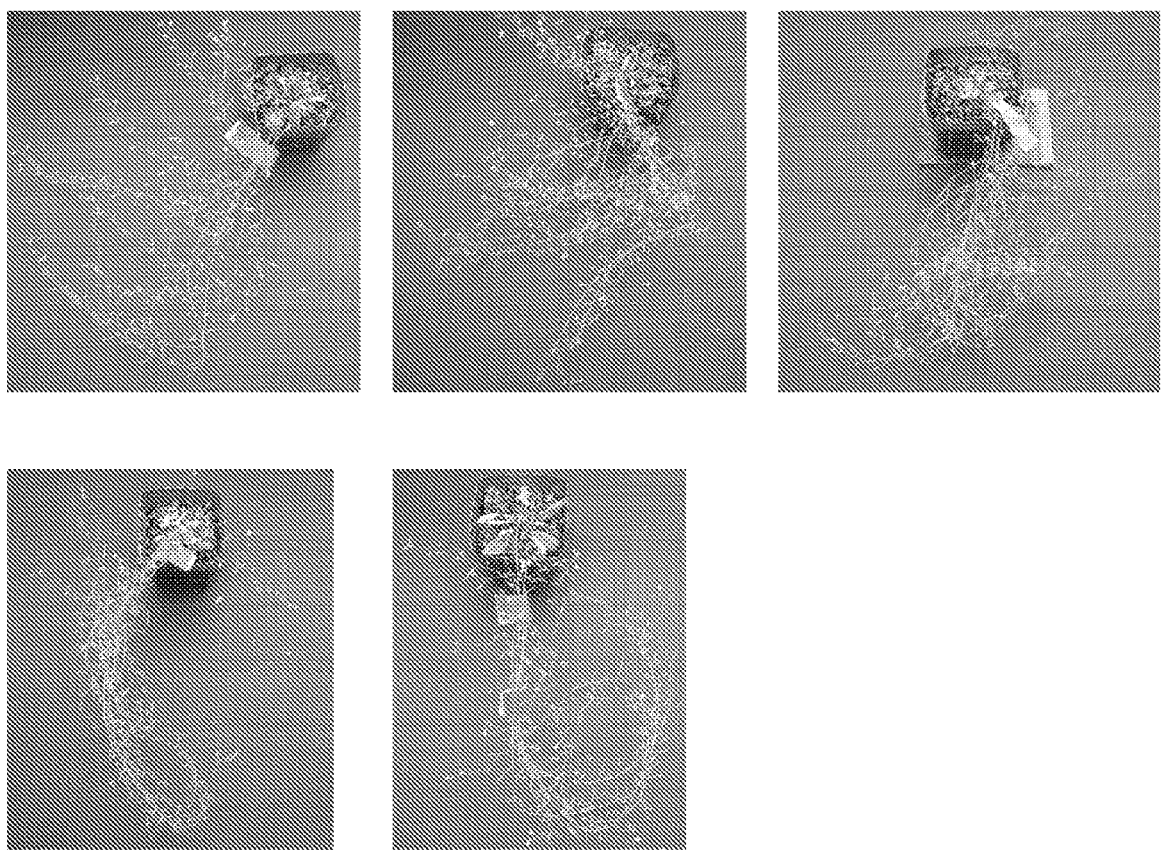

FIG. 16 shows photographs showing states of *Arabidopsis thaliana* plants in which *Escherichia coli*-derived GSH1 was expressed and localized in the chloroplasts.

Figure 17:
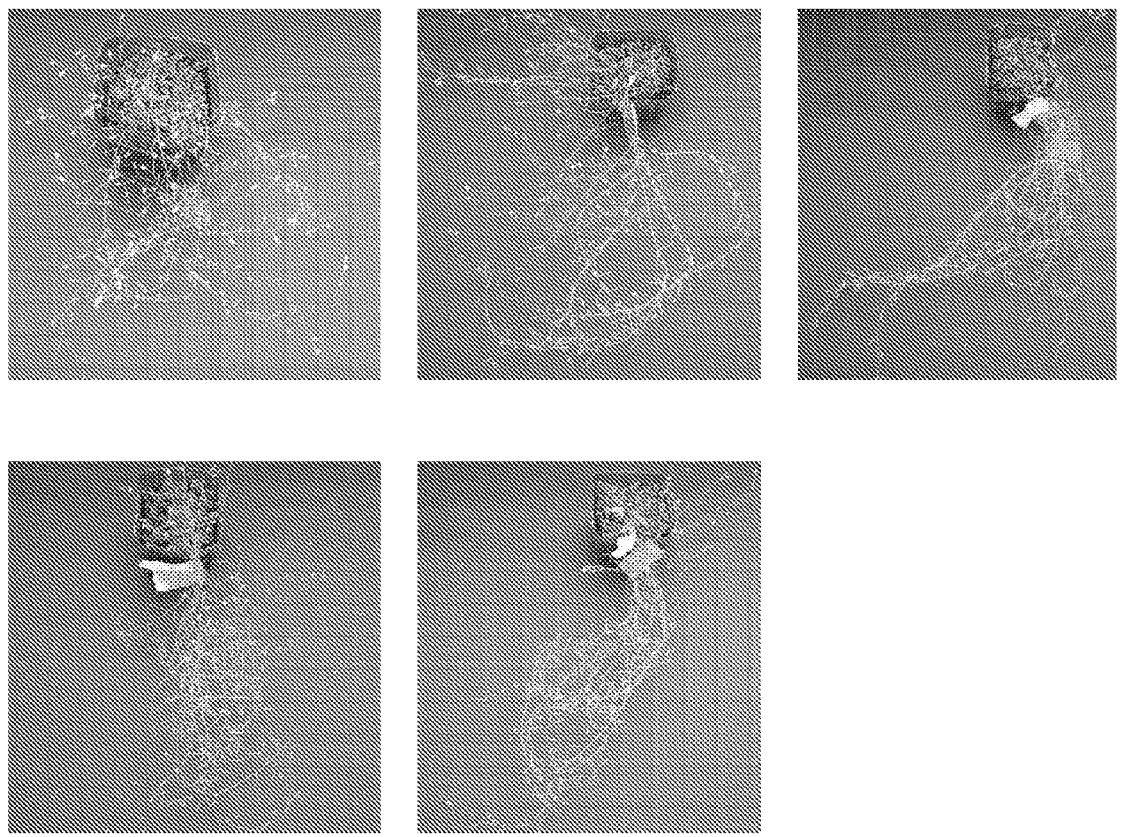

FIG. 17 shows photographs showing states of *Arabidopsis thaliana* plants in which *Escherichia coli*-derived GSH1 was expressed and localized in the cytoplasm.

FIG. 18 shows graphs showing the growth ability and seed yields of plants grown at a light intensity of 200 μE/m$^2$/s.

FIG. 19 illustrates a relationship between (i) a planting density and (ii) growth ability and seed yield per individual (indicated as relative values).

FIG. 20 shows graphs indicating that introduction of GSH1 gene makes it possible to inhibit decreases in biomass quantity, seed yield, and Harvest Index due to an increase in planting density.

Figure 21:
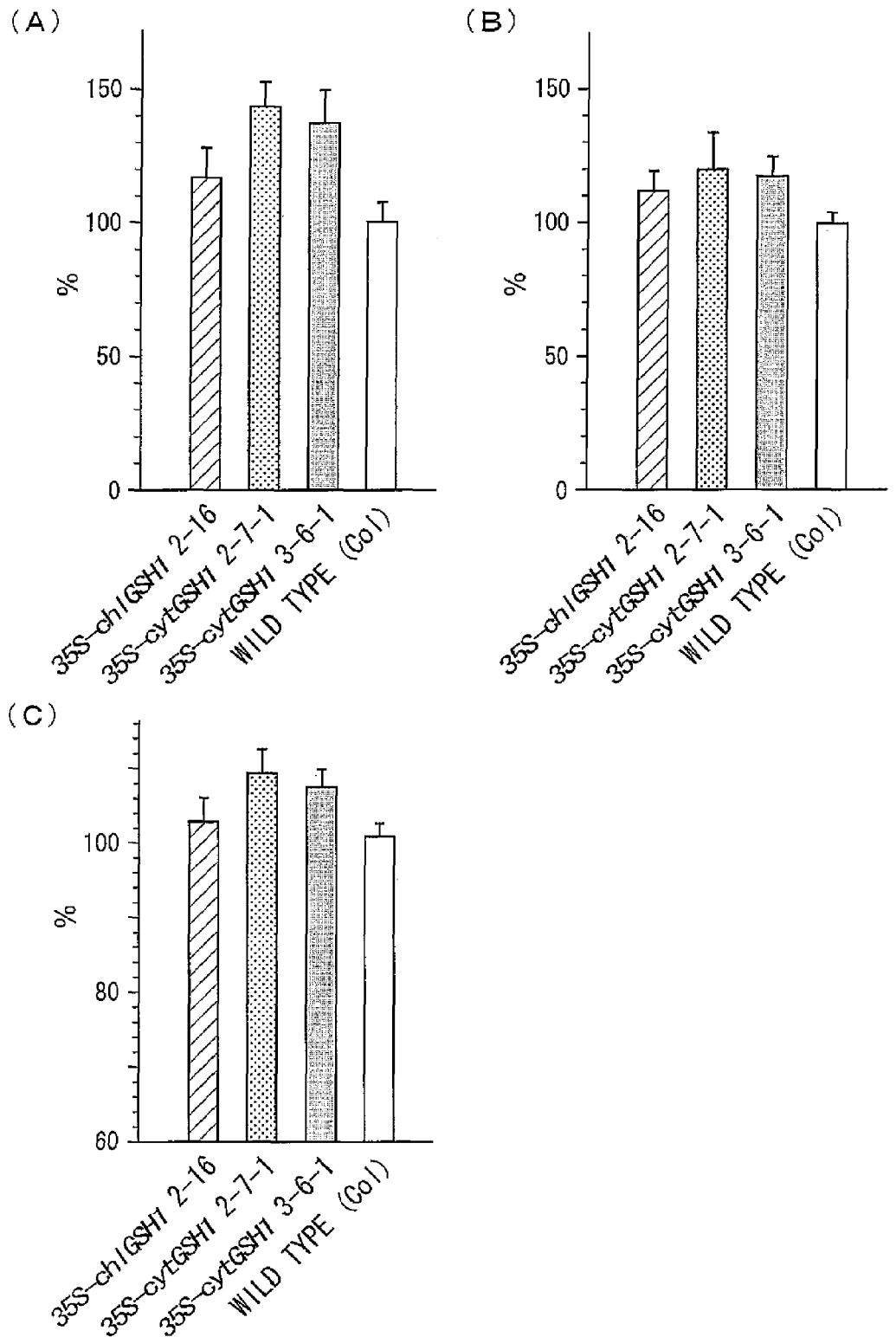

FIG. 21 shows graphs showing differences in yield per unit area and seed weight per unit area among plants in which GSH1 was expressed.

Figure 22:
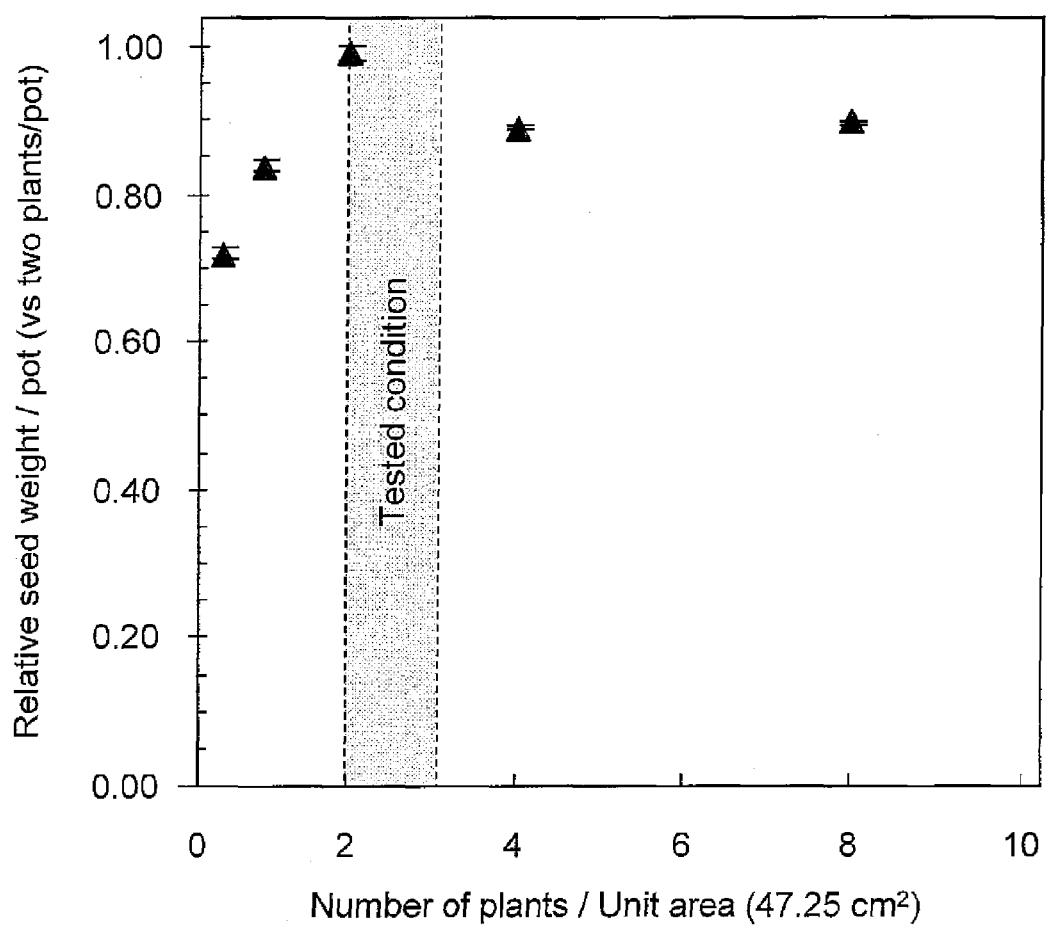

FIG. 22 is a graph showing a relationship between a planting density and seed yield of a wild-type plant.

Figure 23:
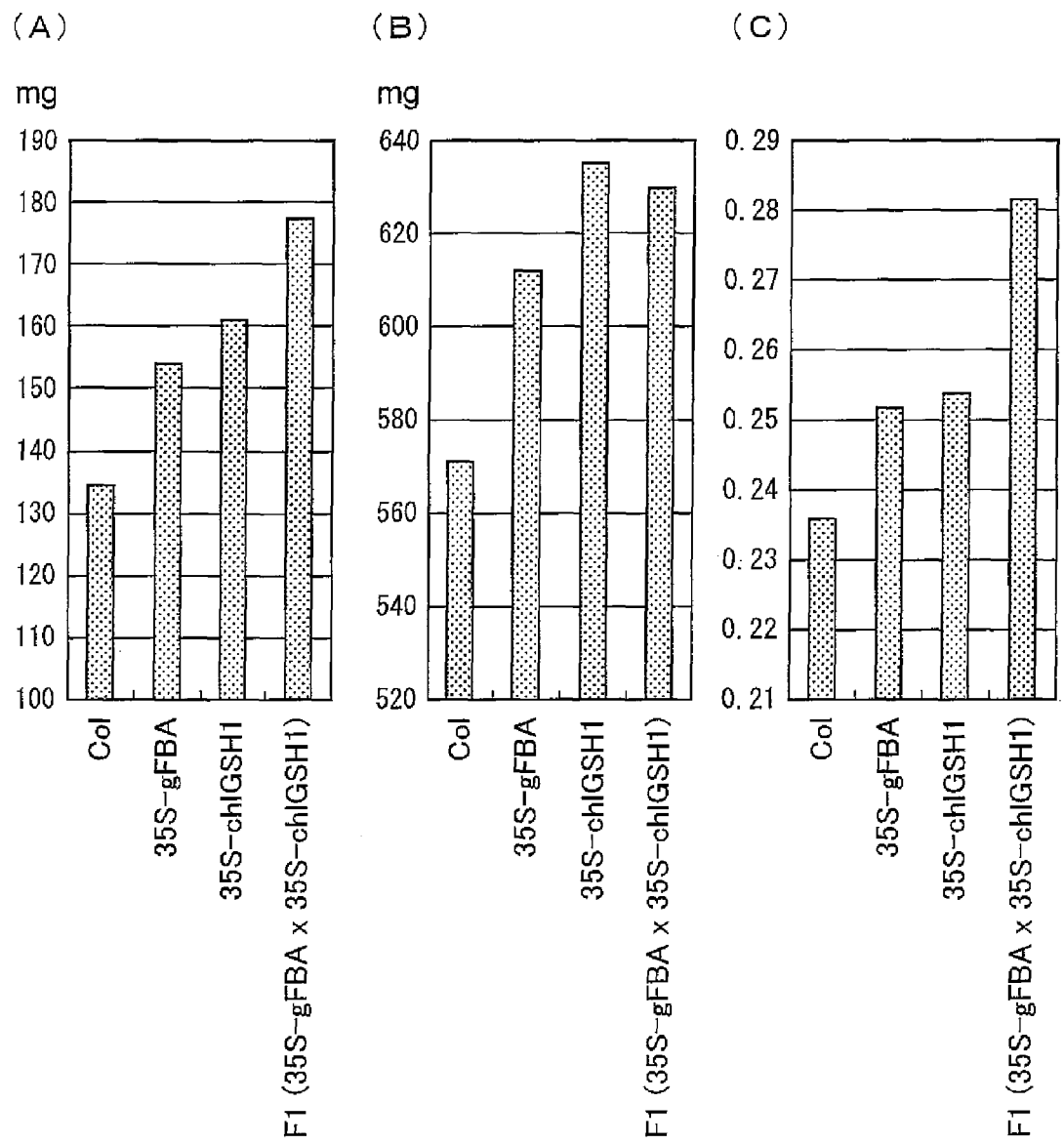

FIG. 23 shows graphs indicating an effect of introduction of a GSH1 gene in the case of an increase in expression level of glutathione-binding aldolase.

Figure 24:
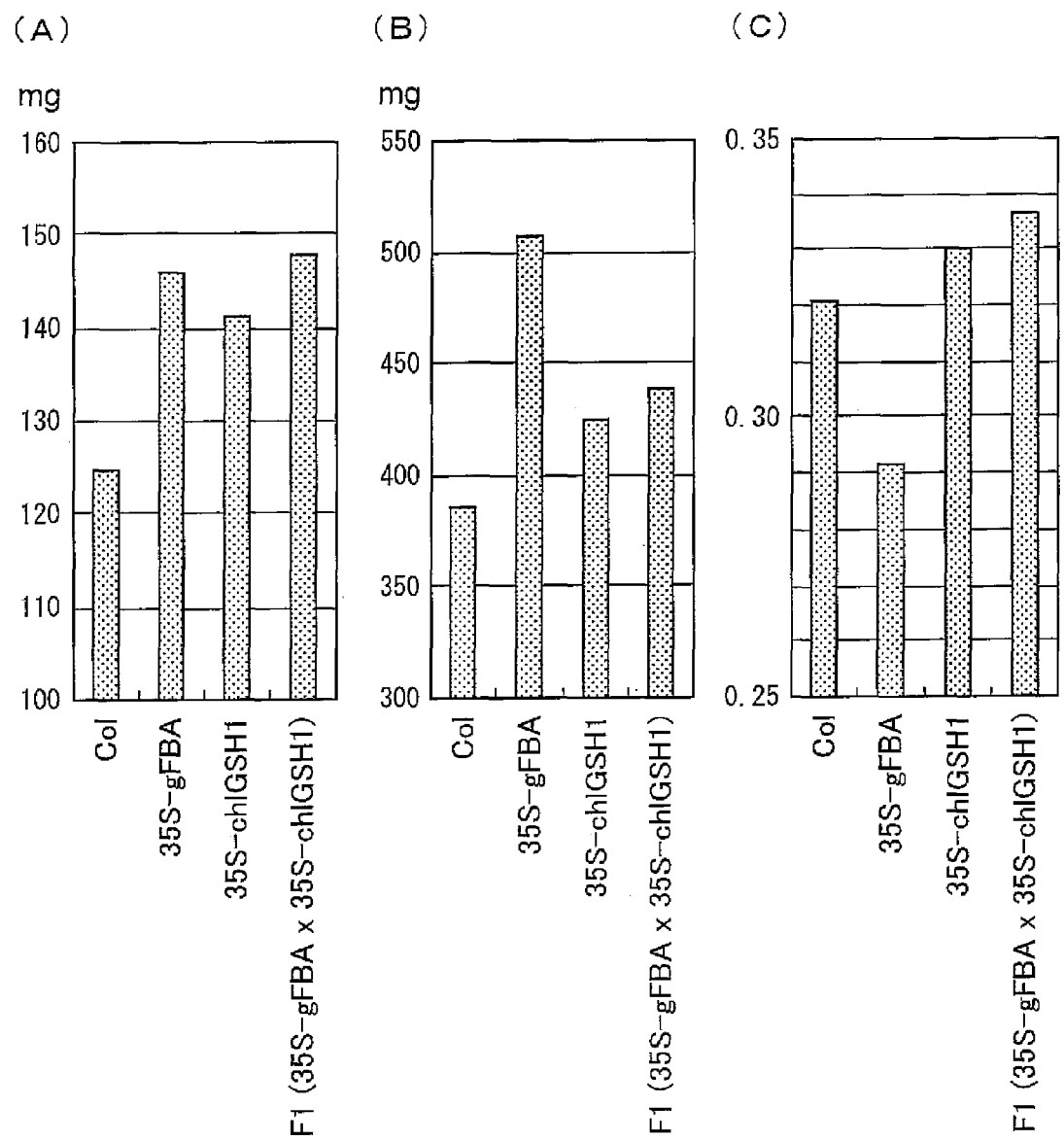

FIG. 24 shows other graphs indicating an effect of introduction of a GSH1 gene in the case of an increase in expression level of glutathione-binding aldolase.

FIG. 25 shows graphs showing the total number of flowers per pot in regard to a chrysanthemum into which 35S-cyt.GSH1-pBI121 was introduced.

DESCRIPTION OF EMBODIMENTS

The present invention provides a plant having a mutation that causes an increase in a level of γ-glutamylcysteine synthetase activity, the plant being further increased in biomass quantity per unit area or seed yield per unit area in comparison with a parent plant thereof, by being cultivated at a planting density higher than that which allows sufficient increases in the biomass quantity per unit area and in the seed yield per unit area.

Further, the present invention provides a plant including a mutation that causes an increase in an expression level of γ-glutamylcysteine synthetase, the plant being further increased in biomass quantity per unit area or seed yield per unit area in comparison with a parent plant, by being cultivated at a planting density higher than that which allows sufficient increases in the biomass quantity per unit area and in the seed yield per unit area.

The plant of the present invention is increased in at least one of the number of flowers, the number of seeds, and the weight of seeds in comparison with those of a parent plant thereof by being cultivated at a planting density higher than that which allows sufficient increases in biomass quantity per unit area and in seed yield per unit area.

The "planting density" means the number of individuals planted per unit area. Generally, in a case where plants are grown, seedlings or young plants are planted or thinned at appropriate intervals. This is because when a planting density for individuals increases, the biomass productivity per individual decreases and the biomass productivity per unit area levels off. As such, each plant has a planting density appropriate for its biomass productivity per unit area. Planting of the plant at a planting density higher than the appropriate planting density causes a decrease in crop yields with respect to purchases costs of seeds or seedlings, and therefore such planting is not preferable. In the present invention, the "planting density which allows sufficient increases in biomass quantity per unit area and in seed yield per unit area" means an optimal planting density for each breed (that is, an optimal planting density at which the biomass productivity per unit area is largest). Although the optimal planting density varies depending on the breed of plant, a person skilled in the art can easily know an optimal planting density for each plant to be used. Even in a case where the plant according to the present invention is cultivated at a planting density higher than that which allows sufficient increases in biomass quantity per unit area and in seed yield per unit area, the biomass quantity per unit area or the seed yield per unit area is further increased in comparison with that of a parent plant/wild-type plant. The planting density at which the plant of the present invention is cultivated is not limited to one higher than the optimal planting density. The planting density is preferably not less than 30%, more preferably not less than 60%, further preferably not less than 100% of the optimal planting density for each breed.

In the present invention, the "γ-glutamylcysteine synthetase activity" means the activity of catalyzing a reaction of an amid bond formation at a γ position of glutamic acid with cysteine.

A level of γ-glutamylcysteine synthetase activity can be found as follows, for example: a plant body is crushed under nitrogen atmosphere as anti-oxidation measure. A solution which contains the crushed plant body therein is centrifuged to give a supernatant as a sample. The sample is added to a reaction solution containing cysteine, glutamic acid, and ATP, so that γ-glutamylcysteine is synthesized. The level of γ-glutamylcysteine synthetase activity is found as an amount of the γ-glutamylcysteine synthesized for a given length of time. As another method, it is also possible to find the level of γ-glutamylcysteine synthetase activity by measuring an amount of phosphoric acid generated along with the reaction.

The "increase in a level of γ-glutamylcysteine synthetase activity" means that the level of γ-glutamylcysteine synthetase activity of a plant is higher than that of a parent plant of the same breed. The activity level of γ-glutamylcysteine synthetase of the plant is compared with that of γ-glutamylcysteine synthetase at a corresponding part in the parent plant of the same breed cultured under the same condition. A case where the activity level of the plant is 1.1 times or more as high as that of the parent plant is preferably considered as a case where the activity level has increased. Here, it is more preferable that the active level of the plant has a significant difference of 5% by a t-test compared with that of the parent plant, in order to be considered that there is an increase in the active level. It is necessary that the activity levels of the plant and the parent plant be measured at the same time by the same method.

In the present invention, the "expression level of γ-glutamylcysteine synthetase" means an amount of γ-glutamylcysteine synthetase mRNA or an amount of γ-glutamylcysteine synthetase protein.

A method for measuring a level of γ-glutamylcysteine synthetase mRNA is not especially limited provided that the method can measure a specific mRNA level, and a conventional method can be used as appropriate. Specifically, examples of the method encompass an RT-PCR method, a real-time RT-PCR method, a competitive PCR method, a northern blot method, an in Situ hybridization method, an in Situ PCR method, a DNA array method, and the like.

A method for measuring a level of γ-glutamylcysteine synthetase protein is not especially limited provided that the method can measure a specific protein level, and a conventional method can be used as appropriate. The method may be, for example, a method using an antibody that specifically binds to the γ-glutamylcysteine synthetase protein to be measured. Examples of the conventional method for measuring a protein level by use of an antibody encompass: a radioimmunoassay (RIA) method; an ELISA method (a solid-phase enzyme-linked immunosorbent assay method); a western blot method; an immunoprecipitation method; an immunohistochemical method; an antibody array method, and the like.

The "increase in an expression level of γ-glutamylcysteine synthetase" means that a plant is increased in the mRNA level or the protein level in comparison with an expression level of γ-glutamylcysteine synthetase of a parent plant of the same breed. The expression level of γ-glutamylcysteine synthetase is compared with that of γ-glutamylcysteine synthetase at a corresponding part in the parent plant of the same breed cultured under the same condition. A case where the expression level increases at least 1.1 times greater than that of the parent plant is preferably considered as a case where the expression level is increased. Here, it is more preferable that the expression level of the plant has a significant difference of 5% by a t-test compared with that of the parent plant, in order to be considered that there is an increase in the expression level. It is preferable that the expression levels of the plant and the parent plant be measured at the same time by the same method. However, data stored as background data may be also used.

In the present invention, "the number of flowers" means the number of flowers of a single individual or plants planted per unit area.

Further, "the number of seeds" means the number of seeds of a single individual or plants planted per unit area.

The "increase in the number of flowers" means that a plant increases in the number of flowers in comparison with that of a parent plant of the same breed cultivated under the same condition. Further, the "increase in the number of seeds" means that the plant increases in the number of seeds in comparison with that of a parent plant of the same breed cultivated under the same condition.

The increase in the number of flowers makes, for example, the value of an ornamental plant whose flowers are to be enjoyed. Further, the increase in the number of flowers leads to an increase in fruits, thereby enhancing the utility value of a plant that bears fruits. Furthermore, the increase in the number of seeds enhances the value of a plant whose seeds are utilized.

A plant having an increased level of γ-glutamylcysteine synthetase activity can be obtained, for example, in such a manner that a mutation is randomly introduced into target plants by use of a conventional mutation introduction method, and screening of the target plants are carried out so as to give an individual having an increased level of γ-glutamylcysteine synthetase.

Similarly, a plant having an increased expression level of γ-glutamylcysteine synthetase can be obtained in such a manner that a mutation is randomly introduced into plants and screening of the plants are carried out so as to give an individual having an increased expression level of γ-glutamylcysteine synthetase.

A method for randomly introducing a mutation into plants is not especially limited, and a conventional method can be used as appropriate. Specifically, examples of the method can be a method for treating seeds with a chemical substance (for example, EMA, NTG, or the like), a method using radiation, a method using transposon, a method using T-DNA, a method for physically introducing a mutation by use of a gene gun, and the like.

As the screening for an individual having an increased level of γ-glutamylcysteine synthetase activity, the aforementioned methods for measuring the level of γ-glutamylcysteine synthetase activity may be used. Similarly, the aforementioned methods for measuring the expression level of γ-glutamylcysteine synthetase may be used as the screening for an individual having an increased expression level of γ-glutamylcysteine synthetase.

Generally, an increase in the expression level of γ-glutamylcysteine synthetase leads to an increase in the level of γ-glutamylcysteine synthetase activity. For this reason, it can be easily understood that a plant having an increased expression level of γ-glutamylcysteine synthetase also has an increased level of γ-glutamylcysteine synthetase activity.

The foregoing description has dealt with a method for obtaining a mutant having an increased activity level or expression level of endogenous γ-glutamylcysteine synthetase. However, a plant having an increased activity level or expression level of γ-glutamylcysteine synthetase can be obtained by introducing a polynucleotide encoding plant-derived γ-glutamylcysteine synthetase. That is, the present invention provides a transformed plant which has incorporated a polynucleotide encoding plant-derived γ-glutamylcysteine synthetase and which is increased in at least either the number of flowers or the number of seeds. The following deals with a transformed plant according to the present invention and a method according to the present invention for increasing at least either the number of flowers or the number of seeds of a plant.

In the present specification, the term "polypeptide" is used interchangeably with "peptide" or "protein". Further, in the present specification, the term "polynucleotide" is used interchangeably with "gene", "nucleic acid", or "nucleic acid molecule", and means a polymer of nucleotide.

The polynucleotide (hereinafter, referred to as "GSH1 gene"), for use in the present invention, which encodes γ-glutamylcysteine synthetase is not especially limited provided that the γ-glutamylcysteine synthetase that the polynucleotide encodes is derived from a plant. The polynucleotide is preferably a GSH1 gene included in a host plant, but a GSH1 gene derived from a plant different from the host plant can be also preferably used.

It was observed that, in a case where a translated product of the plant-derived GSH1 gene for use in the present invention has a chloroplast targeting signal peptide, the transformed plant of the present invention increases in at least either the number of flowers or the number of seeds, and further increases in biomass quantity and seed yield. On the other hand, it was observed that, in a case where a translated product of the plant-derived GSH1 gene for use in the present invention has no chloroplast targeting signal peptide, the transformed plant of the present invention increases in at least either the number of flowers or the number of seeds, and has an improved harvest index. Phenotypic characteristics of these plants will be described later.

Protein coded for by the plant-derived GSH1 gene generally has a chloroplast targeting signal peptide. Accordingly, a plant-derived GSH1 gene product, that is, a γ-glutamylcysteine synthetase is generally present in a chloroplast. On the other hand, a γ-glutamylcysteine synthetase having no chloroplast targeting signal peptide cannot be transferred to a chloroplast.

In the present specification, the "γ-glutamylcysteine synthetase having no chloroplast targeting signal peptide" means a γ-glutamylcysteine synthetase having no chloroplast targeting signal peptide that functions properly. The γ-glutamylcysteine synthetase having no chloroplast targeting signal peptide encompasses: one that lacks an entire chloroplast targeting signal peptide region that is normally present; one that partially lacks a chloroplast targeting signal peptide region and lost a chloroplast targeting function; one that lost a chloroplast targeting function due to substitution or addition of amino acids; one that normally has no chloroplast targeting signal peptide; and the like.

On this account, it is necessary that the GSH1 gene encoding a γ-glutamylcysteine synthetase having no chloroplast targeting signal peptide be artificially produced, for example, as a mutated GSH1 gene that lacks a region encoding a chloroplast targeting signal peptide.

A preferable example of the GSH1 genes for use in the present invention is a GSH1 gene (TAIR Accersion Gene: 2127172, Name AT4G23100.1) of *Arabidopsis thaliana*, which the inventors of the present invention used. A γ-glutamylcysteine synthetase of *A. thaliana* has the amino acid sequence represented by SEQ ID NO: 1, and a gene (full-length cDNA) encoding the γ-glutamylcysteine synthetase has the base sequence represented by SEQ ID NO: 5. The codon from the position 172 to 174 is an initiation codon and the termination codon is the codon from positions 1738 through 1740 in the base sequence represented by SEQ ID NO: 5. That is, the *A. thaliana* GSH1 gene includes part of the base sequence represented by SEQ ID NO: 5 which starts at position 172 and ends at position 1740 and which acts as an open reading frame (ORF) for the *A. thaliana* GSH1 gene. The base sequence represented by SEQ ID NO: 2 is the base sequence of the ORF of the *A. thaliana* GSH1 gene.

Further, in the case of a product (a polypeptide having the amino acid sequence represented by SEQ ID NO: 1) of the *A. thaliana* GSH1 gene, it was observed by the inventors of the present invention that deletion of 73 amino acids from the N-terminal side causes γ-glutamylcysteine synthetase to remain in cytoplasm without being transferred to chloroplast. Herein, an example of a γ-glutamylcysteine synthetase of *A. thaliana*, the γ-glutamylcysteine synthetase having no chloroplast targeting signal peptide, is a polypeptide having the amino acid sequence represented by SEQ ID NO: 3, and a gene encoding the γ-glutamylcysteine synthetase having no chloroplast targeting signal peptide has the base sequence represented by SEQ ID NO: 4. An amino acid to be deleted is not limited to the 73 amino acids from the N-terminal side, but can be selected as appropriate provided that a function of the chloroplast targeting signal peptide is hindered by the deletion. A person skilled in the art can easily check, by use of a publicly-known technique, what kind of gene modification causes a hindrance to the function of the chloroplast targeting signal peptide.

Known examples of plant-derived GSH1 genes other than the *A. thaliana* GSH1 gene encompass a gene of *Zinnia elegans* (Genbank accession: AB158510), a gene of *Oryza sativa* (Genbank accession: AJ508915), a gene of *Nicotiana tabacum* (Genbank accession: DQ444219), and the like. These genes can be also preferably used in the present invention. Translated products of these genes also have a chloroplast targeting signal peptide in the N-terminal region, similarly to that of *A. thaliana*.

Moreover, a polynucleotide encoding a polypeptide (i) having an amino acid sequence in which one or several amino acids are deleted, substituted, or added from/in/to the amino acid sequence represented by SEQ ID NO: 1 or 3, and (ii) having γ-glutamylcysteine synthetase activity can be preferably used in the present invention.

Here, the expression "one or several amino acids are deleted, substituted, or added" means that an amino acid(s) is/are deleted, substituted, or added to the extent that the amino acid(s) (preferably not more than 10, more preferably not more than 7, further preferably not more than 5 amino acids) are deleted, substituted, or added from/in/to the amino acid sequence by a well-known peptide mutant production method such as a site-directed mutagenesis method. Such a protein mutant obtained in the above manner is not limited to an artificially-mutated protein mutant produced by the well-known polypeptide mutant production method, but may be a naturally-occurred protein mutant obtained by isolating it from among natural proteins.

It has been well known in the related field of the present invention that several amino acids in an amino sequence of a protein can be easily modified without significantly affecting the structure or function of the protein. Further, it has been also well known that some natural proteins have mutants that do not significantly change the structures or functions of these natural proteins.

Preferable mutants have conservative or nonconservative substitution, deletion, or addition of amino acids. Silent substitution, addition, and deletion are preferred, and conservative substitution is especially preferred. These mutations do not change polypeptide activity of the present invention.

Typical conservative substitutions encompass: substitution of one of aliphatic amino acids Ala, Val, Leu, and Ile with another amino acid; exchange of hydroxyl residues Ser and Thr; exchange of acidic residues Asp and Glu; substitution between amide residues Asn and Gln; exchange of basic residues Lys and Arg; and substitution between aromatic residues Phe and Tyr.

Further, in the present invention, a polynucleotide that hybridizes, under a stringent condition, with the polynucleotide having the base sequence represented by SEQ ID NO: 2 or 4 can be used, as long as the polynucleotide can encode a protein having the γ-glutamylcysteine synthetase activity. Such a polynucleotide encompass, for example, a polynucleotide encoding a polypeptide having an amino acid sequence in which one or several amino acids are deleted, substituted, or added from/in/to the amino acid sequence represented by SEQ ID NO: 1.

In the present invention, the "stringent condition" means that hybridization occurs only when sequences share at least 90%, preferably at least 95%, most preferably at least 97% similarity with each other. More specifically, the stringent condition may be a condition where polynucleotides are incubated in a hybridization solution (50% formamide, 5×SSC [150 mM NaCl, 15 mM trisodium citrate], 50 mM sodium phosphate [pH 7.6], 5×Denhart's solution, 10% dextran sulfate, and 20 µg/ml of sheared denatured salmon sperm DNA) overnight at 42° C., and then the filter is washed with 0.1× SSC at about 65° C.

The hybridization can be carried out by well-known methods such as a method disclosed in Sambrook et al., Molecular Cloning, A Laboratory Manual, 3rd Ed., Cold Spring Harbor Laboratory (2001). Normally, stringency increases (hybridization becomes difficult) at a higher temperature and at a lower salt concentration. As stringency increases more, a more homologous polynucleotide can be obtained.

Similarity between amino acid sequences or between base sequences can be determined by use of an algorithm BLAST according to Karlin and Altschul (Karlin S, Altsuchul S F, Proc. Natl. Acad. Sci. USA, 87: 2264-2268 [1990]; Karlin S, Altschul S F, Proc. Natl. Acad Sci. USA, 90: 5873-5877 [1993]). Programs based on the algorithm BLAST, called BLASTN and BLASTX, have been developed (Altschul S F, et al., J. Mol. Biol., 215: 403 [1990]).

The GSH1 gene for use in the present invention may derived from a genomic DNA or cDNA, and may be a chemosynthetic DNA. Further, the GSH1 gene may be RNA.

A method for obtaining the GSH1 gene for use in the present invention may be a method for isolating and cloning, by use of a well-known technique, a DNA fragment encoding γ-glutamylcysteine synthetase. For example, the method may be such that a probe that specifically hybridizes with part of a base sequence of DNA encoding γ-glutamylcysteine synthetase of *A. thaliana* is prepared and a genomic DNA library or a cDNA library is screened with the probe.

Alternatively, the method for obtaining the GSH1 gene for use in the present invention can be a method using amplification means such as PCR. For example, primers are prepared respectively from sequences on the 5' side and the 3' side (or their complementary sequences) of cDNA encoding γ-glutamylcysteine synthetase of *A. thaliana*. Then, PCR or the like is performed with use of the primers and a genomic DNA (or cDNA) as a template, so as to amplify a DNA between the annealed primers. This makes it possible to obtain a great amount of DNA fragments (GSH1 genes) encoding γ-glutamylcysteine synthetase, for use in the present invention.

The GSH1 gene for use in the present invention can be obtained from tissue or cells of an appropriate plant as a source. Since all plants have a GSH1 gene, a GSH1 gene for use in the present invention may be obtained from an intended plant as a source.

In the present invention, a preferable method to be used as a method for introducing a GSH1 gene into a plant can be a method such that a recombinant expression vector in which a promoter functioning in a plant cell is connected upstream of DNA encoding γ-glutamylcysteine synthetase and a terminator functioning in a plant cell is connected downstream of the DNA is constructed and introduced into a plant.

In the after-mentioned Examples, a cauliflower mosaic virus 35S promoter that induces constitutive gene expression is used as a promoter functioning in a plant cell, but the promoter is not limited to this. Examples of a constitutive promoter other than the cauliflower mosaic virus 35S promoter can be an actin promoter of Oryza, a ubiquitin promoter of Maize, and the like. These promoters can be preferably used in the present invention.

Examples of a promoter other than the constitutive promoter may be chloroplast tissue-specific promoters such as an rbcS promoter and a Cab promoter, inducible promoters such as an HSP70 promoter, and the like, but the promoter is not limited to these. Further, an rbcL promoter and the like promoters can be used as a promoter to be directly inserted into a chloroplast genome, but the promoter is not limited to these provided that the promoter functions in a chloroplast.

Examples of the terminator functioning in a plant cell can be a terminator derived from a nopaline synthetase (NOS) gene, a terminator derived from cauliflower mosaic virus, and the like terminators.

A recombinant expression vector for use in transformation of a plant is not especially limited provided that the recombinant expression vector can express an inserted gene in a plant cell. Especially, in a case where a method using *Agrobacterium* is adopted as a method for introducing a vector into a plant, it is preferable to use a binary vector of a pBI system or the like. Examples of the binary vector encompass: pBIG, pBIN19, pBI101, pBI121, pBI221, and the like.

A target plant to be transformed in the present invention encompasses a whole plant, a plant organ (e.g., a leaf, a petal, a stem, a root, a seed), plant tissue (e.g., epidermis, phloem, parenchyma, xylem, bundle, palisade layer, spongy tissue), a cultured plant cell, a variously-altered plant cell (e.g., suspension-cultured cell), a protoplast, a section of a leaf, callus, and the like. The plant for use in transformation is not especially limited, and a plant in which a GSH1 gene to be used can be expressed may be selected as appropriate.

In a case where the *A. thaliana* GSH1 gene is used, the target plant to be transformed is preferably plants of Brassicaceae closely related to *A. thaliana*, but is not limited to this. It has been reported that transformed plants of tobacco, poplar, lemon, and the like plants can be produced by the *A. thaliana* gene (Franke R, McMichael C M, Meyer K, Shirley A M, Cusumano J C, Chapple C. (2000) Modified lignin in tobacco and poplar plants over-expressing the *Arabidopsis* gene encoding ferulate 5-hydroxylase. Plant J. 22: 223-234; Pena L, Martin-Trillo M, Juarez J, Pina J A, Navarro L, Martinez-Zapater J M. (2001) Constitutive expression of *Arabidopsis* LEAFY or APETALA1 genes in citrus reduces their generation time. Nat. Biotechnol. 19: 263-267). On this account, it is considered that introduction of the *A. thaliana* GSH1 gene into such a plant allows producing a transformed plant increased in at least either the number of flowers or in the number of seeds.

Introduction of a recombinant expression vector into a plant cell is carried out by a transformation method well known by a person skilled in the art (for example, an *Agrobacterium* method, a particle gun method, a polyethylene glycol method, an electroporation method, and the like). In a case where the *Agrobacterium* method is used, for example, a transformed plant can be obtained by introducing a constructed plant expression vector into appropriate *Agrobacterium* (for example, *Agrobacterium tumefaciens*), and then infecting the strain with an aseptically-cultured lamina by a leaf disc method (Hirofumi UCHIMIYA, "*Shokubutsu Idenshi Sousa Manual*" (Plant Genetic Manipulation Manual), 1990, 27-31 pp, Kodansha Scientific, Tokyo), or the like method.

Further, in a case where the particle gun method is used, an individual plant, a plant organ, and plant tissue may be directly used, or alternatively they may be used after they are sectioned to pieces or protoplasts thereof are prepared. A sample so prepared can be processed by use of a gene-introduction device (for example, PDS-1000, manufactured by BIO-RAD). Processing conditions vary depending on the plant or the sample, but are generally as follows: a pressure of about 450 to 2000 psi, and a distance of 4 to 12 cm.

Cells or plant tissue into which an intended gene has been introduced are screened with the use of a drug-resistant marker such as a kanamycin-resistant marker or a hygromycin-resistant marker, and the cell or plant tissue thus screened is regenerated into an individual plant in accordance with a usual method. Regeneration from the transformed cell to an individual plant can be carried out by a person skilled in the art by use of a publicly known method depending on the type of the plant cell.

Confirmation of whether or not an intended gene has been introduced into a plant can be carried out by a PCR method, a southern hybridization method, a northern hybridization method, or the like method. For example, DNA is prepared from a transformed plant, and primers specific to the introduced DNA are designed, and PCR is performed. After that, amplification products are subjected to agarose gel electrophoresis, polyacrylamide gel electrophoresis, or capillary electrophoresis, and then stained with ethidium bromide so that an intended amplification product is detected, whereby the transformation can be confirmed.

Once the transformed plant that has incorporated the GSH1 gene in its genome can be obtained, it is possible to obtain progeny from the plant by sexual reproduction or asexual reproduction. Further, it is possible to carry out massproduction of an intended plant from a reproductive material (for example, seeds or protoplasts) obtained from the plant or its progeny or clone.

The transformed plant (that is, the transformed plant of the present invention) thus obtained is cultivated at a planting density higher than that which allows sufficient increases in biomass quantity per unit area and in seed yield per unit area. The transformed plant cultivated in such a manner is increased in at least either the number of flowers or the number of seeds, in comparison with a parent plant (a plant used for the transformation).

It was observed that, among the plants according to the present invention, a plant having an increased expression level of γ-glutamylcysteine synthetase with a chloroplast targeting signal peptide and having an increased level of γ-glutamylcysteine synthetase activity is increased in at least either the number of flowers or the number of seeds and is further increased in biomass quantity and seed yield in comparison with the parent plant. Such a plant encompasses: a plant having an increased expression level of γ-glutamylcysteine synthetase having a chloroplast targeting signal peptide due to artificial mutagenesis or natural mutation; and a transformed plant into which a polynucleotide encoding γ-glutamylcysteine synthetase having a chloroplast targeting signal peptide has been introduced.

In the present specification, the "biomass quantity" means the dry weight of an individual plant. Further, the "seed yield" means the weight of all seeds of a single individual plant or seed yield per unit area.

An increase in biomass quantity brings about various advantages as follows: the means that a larger quantity of carbon dioxide is fixed as carbohydrate, the amount of $CO_2$ in the atmosphere is efficiently decreased because the increase in biomass quantity means that a larger quantity of $CO_2$ is fixed as carbohydrate; in case of vegetables, edible portions of the vegetables is grown larger, thereby expanding food production; and in case of woods, the increase in biomass quantity means that production of raw materials for paper etc. is enlarged. Further, the increase in seed yield can realize a large increase in the yield of seeds of foods crops and energy crops. This advantageously contributes to a large reduction in production costs.

It was observed that, among the plants of the present invention, a plant in which γ-glutamylcysteine synthetase having no chloroplast targeting signal peptide has been expressed is increased in at least either the number of flowers or the number of seeds and is further improved in harvest index in comparison with its parent plant. Such a plant encompass: a plant in which not only a γ-glutamylcysteine synthetase originally having a chloroplast targeting signal peptide but also a γ-glutamylcysteine synthetase having no chloroplast targeting signal peptide have been expressed due to artificial mutagenesis or natural mutation; and a transformed plant into which a polynucleotide encoding γ-glutamylcysteine synthetase having no chloroplast targeting signal peptide has been introduced.

In the present invention, the "harvest index" means a value calculated by dividing "the weight of all seeds of an individual plant" by "the dry weight of the individual plant including the seed weight".

An increase in harvest index leads to an increase in seed yield per unit area, thereby bringing about such an advantage that a crop yield efficiently increases especially in a land limited in nutrients.

The transformed plant of the present invention may further have incorporated a polynucleotide (a glutathione-binding aldolase gene) encoding glutathione-binding aldolase. The inventors of the present invention have found that a transformed plant having incorporated DNA encoding glutathione-binding aldolase has an improved growth ability and an improved disease resistance (WO2007/091634). However, although the transformed plant having incorporated the glutathione-binding aldolase gene has an improved growth ability, the harvest index thereof is not necessarily improved and it depends on light conditions. Introduction of the GSH1 gene and the glutathione-binding aldolase gene allows a further improvement in the harvest index and the seed yield of a plant. A person skilled in the art who has read this specification can easily understand that means for introducing the glutathione-binding abdolase may be carried out in accordance with the aforementioned means for introducing the GSH1 gene.

The embodiments of implementation discussed in the foregoing detailed explanation and concrete examples described as follows serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Further, all the academic literatures and patent literatures cited in the present specification are incorporated in the present specification as references.

EXAMPLES

The present invention is described as follows in more detail with reference to Examples. However, the present invention is not limited to the following Examples.

(1) Plants Used

A parent plant used for producing a transformant was wild-type *Arabidopsis thaliana* (Columbia, Col-0). The plants were seeded in a square-shaped plastic pot (6.5×6.5×5 cm) filled with three-layer soil having layers of vermiculite (Asahi Kogyo, Inc., Okayama), Kureha culture soil (Kureha garden cultivating soil, Kureha Co., Tokyo), and vermiculite in this order from the bottom at a ratio of 2:2:1, and grown under a long-day condition (16-hour light period/8-hour dark period) at a growth temperature of 22° C.

(2) Cloning of GSH1 Gene, Alteration of GSH1 Gene, and Production of GSH1 Transformant Total RNA was isolated from three-week old *A. thaliana* (wild-type Columbia, (Col-0)), and cDNA was synthesized with use of Prostar first strand RT-PCR kit (Stratagene, La Jolla, Calif., USA).

As shown in an upper part of A of FIG. 1 (Chl.GSH1), the following specific primers designed based on a cDNA sequence of GSH1 were used for amplifying a full-length cDNA as two fragments through PCR. Then, each of the amplified fragments was sub-cloned to a pGEM-T Easy vector (Promega, Madison, Wis., USA). The primers GSH1_5'-3 and GSH1_3'-2 incorporated cleavage sites of Xba I and Sac I respectively, the cleavage sites being required for the primers to be introduced to a binary vector pBI121 for transformation of a plant (the underlines in the following sequences indicate substituted bases).

```
Chem. 1
                                            (SEQ ID NO: 6)
    GSH1_5'-3:    5'-GCTTTCTTCTAGATTTCGACGG-3'
    GSH1_3'-3:    5'-CCTGATCATATCAGCTTCTGAGC-3'

(SEQ ID NO: 7)
    GSH1_5'-2:    5'-ATGCCAAAGGGGAGATACGA-3'
    GSH1_3'-2:    5'-GGAGACTCGAGCTCTTCAGATAG-3'
```

The two fragments were fused at a cleavage site of Kpn I to give a vector (Chl.GSH1-pGEM) containing full-length cDNA. The Chl.GSH1-pGEM was treated with restriction enzymes Xba I and Sac I, and the obtained fragment was replaced with a region encoding β-glucuronidase (GUS), the region being located downstream of a cauliflower mosaic virus 35S promoter of the binary vector pBI121. In this manner, a construct (35S-Chl.GSH1-pBI121) for producing a transformed plant was produced (see B of FIG. 1).

An *A. thaliana* genome has only one copy of GSH1 gene thereon, and the GSH1 gene contains a chloroplast targeting signal. In view of this, in order to accumulate a GSH1 gene product (γ-glutamylcysteine synthetase) in cytoplasm, a construct (35S-cyt.GSH1-pBI121) for expressing protein in which the first 73 amino acids from the N-terminal (which 73 amino acids were suspected to be a chloroplast targeting signal) were deleted and a 74th alanine residue from the N-terminal was substituted with a methionine residue was produced. First, PCR was performed with use of (i) the following primer GSH1 (cyt.)_5' in which the 74th alanine residue from the N-terminal was substituted with the methionine residue and the Xba I cleavage site was inserted upstream of the substituted part (the base substitution sites are indicated by underlines) and (ii) the above-described GSH1_3'-3 (see middle part of A of FIG. 1). Next, the obtained fragment was treated with the restriction enzymes Xba I and Kpn I, and then sub-cloned to a pBluescript vector (Stratagene, La Jolla, Calif., USA) (cyt.GSH1-pBS).

```
Chem. 2
                                            (SEQ ID NO:
GSH1 (cyt.)_5':    5'-AGGGCATCTAGAGACCATGGCAAGTCC-3'
```

After the cyt.GSH1-pBS was treated with the restriction enzymes Xba I and Kpn I, the obtained fragment was replaced with an Xba I-Kpn I fragment on GSH1 of the 35S-Chl.GSH1-pBI121, thereby producing the 35S-cyt.GSH1-pBI121 (see B of FIG. 1).

Further, in order to improve the stability of mRNA of the GSH1 gene, 35S-5'UTRcyt.GSH1-pBI121 having a 5'-untranslated region (64 bp) of the GSH1 gene was produced. First, an Xba I-Nco I fragment on the Chl.GSH1-pGEM was replaced with an Xba I-Nco I fragment on the cyt.GSH1-pBS (5'UTRcyt.GSH1-pBS). Next, the 5'UTRcyt.GSH1-pBS was treated with the restriction enzymes Xba I and Kpn I. Then, the obtained fragment was replaced with the Xba I-Kpn I fragment on the 35S-Chl.GSH1-pBI121, thereby producing the 35S-5'UTRcyt.GSH1-pBI121 (see B of FIG. 1).

Furthermore, in order to produce a transformed plant in which *Escherichia coli*-derived γ-glutamylcysteine synthetase is excessively accumulated, a construct (35S-EcGSH1-pBI121) for transformation was produced by cloning a GSH1 gene from *E. coli* (DH5α). The construct was expected to accumulate in the cytoplasm. In view of this, in order to accumulate the *E. coli*-derived γ-glutamylcysteine synthetase in a chloroplast, a construct (35S-Chl.EcGSH1-pBI121) was also produced. The 35S-Chl.EcGSH1-pBI121 is such that the first 89 amino acids from the N-terminal of the γ-glutamylcysteine synthetase of the *A. thaliana* (the amino acids containing a region suspected as the chloroplast targeting signal of the γ-glutamylcysteine synthetase of the *A. thaliana*) are fused with an N-terminal of the *E. coli*-derived γ-glutamylcysteine synthetase. First, as shown in an upper part of A of FIG. 14 (EcGSH1), with use of an *E. coli* (DH5α) cell as a template, the following set of specific primers EcGSH1_F1 and EcGSH1_R1 and the set of specific primers EcGSH1_F2 and EcGSH1_R2, each of which was designed based on the base sequence of *E. coli* GSH1 (Genbank accession:X03954), were used to perform PCR, through which a full-length GSH1 gene as two fragments were amplified. The obtained fragments were treated with the restriction enzyme Xba I or Sac I, and sub-cloned to a pBluescript vector (Stratagene, La Jolla, Calif., USA) (EcGSH1_FR1-pBS and EcGSH1_FR2-pBS). The primer EcGSH1_F1 (sub-cloned product) incorporated the Xba I cleavage site required for the amplified product to be introduced into the binary vector pBI121 for transformation of a plant and a Hinc II cleavage site required for inserting the chloroplast targeting signal. Further, in order to substitute an initiation codon from a leucine residue to a methionine residue, base substitution was introduced. The primer EcGSH1_R2 (sub-cloned product) incorporated a Sac I cleavage site required for the amplified product to be introduced to the binary victor pBI121 for transformation of a plant (the underlines in the following sequences indicate substituted bases).

```
Chem. 3
                                         (SEQ ID NO: 25)
EcGSH1_F1:   5'-TTTGACAGTCTAGAGTTGACTATGATCCCG-3'
EcGSH1_R1:   5'-TTCCGATGGCGTTTTGATTGCC-3'

(SEQ ID NO: 26)
EcGSH1_F2:   5'-TCGTTTGAGCGATCTCGGCTATACC-3'
EcGSH1_R2:   5'-AATTTTGGGAGCTCACGAGTGGCC-3'
```

The two fragments thus obtained were fused at a SnaB I cleavage site to give a vector (EcGSH1-pBS) containing a full-length GSH1. The EcGSH1-pBS was treated with the restriction enzymes Xba I and Sac I, and the obtained fragment was replaced with a region encoding the β-glucuronidase (GUS), the region being located downstream of the cauliflower mosaic virus 35S promoter of the binary vector pBI121. In this manner, the construct (35S-EcGSH1-pBI121) for producing a transformed plant was produced (B of FIG. 14).

The construct (35S-Chl.EcGSH1-pBI121) to which the chloroplast targeting signal is fused was prepared in a manner described as follows. First, a fragment containing an upstream region of the *E. coli* GSH1 gene, the fragment being obtained by treating the EcGSH1_FR1-pBS with the restriction enzyme Hinc II, was fused with a product made by treating the above-mentioned Chl.GSH1-pGEM containing the full-length cDNA of the *A. thaliana* GSH1 gene with the restriction enzyme Hinc II (Chl.EcGSH1_FR1-pGEM). Next, the Chl.EcGSH1_FR1-pGEM was treated with the restriction enzymes Ava I and Sac I, and then an Ava I-Sac I fragment of the EcGSH1-pBS was inserted to thus treated Chl.EcGSH1_FR1-pGEM (Chl.EcGSH1-pGEM). After the Chl.EcGSH1-pGEM was treated with the restriction enzymes Xba I and Sac I, the obtained fragment was replaced with the region encoding the β-glucuronidase (GUS), the region located downstream of the cauliflower mosaic virus 35S promoter of the binary vector pBI121. In this manner, the construct (35S-Chl.EcGSH1-pBI121) for transformation was produced (see B of FIG. 14).

Each of the five types of expression vectors 35S-Chl.GSH1-pBI121, 35S-cyt.GSH1-pBI121, 35S-5'UTR-cyt.GSH1-pBI121, 35S-EcGSH1-pBI121, and 35S-Chl.EcGSH1-pBI121 produced above was introduced into the Col-0 with use of *Agrobacterium* method (Clough, S. J. and SH1-pB Bent, A. F. (1998) Floral dip: A simplified method for *Agrobacterium*-mediated transformation of *Arabidopsis thaliana*. Plant J. 16: 735-743.), so as to produce a transformed plant.

To be more precise, screening was repeatedly performed on an agar medium (Murashige-Skoog medium in a concentration of 50%) containing kanamycin serving as a selective marker, until all the seeds went into a generation that exhibits kanamycin resistance (a generation in which characters were not segregated). In the course of the screening, it was found that the characters of the kanamycin resistance were segregated at a ratio of 3:1, and that the expression vector was introduced into at least a single chromosome.

(3) Analysis of an Expression Level of GSH1 Gene Through RT-PCR

A transformant into which 35S-Chl.GSH1-pBI121 had been introduced was analyzed for an expression level of GSH1 gene through RT-PCR as described below.

First, total RNA was extracted from aboveground parts of three-week old transformed *A. thaliana* with use of RNeasy Plant Mini Kit (Qiagen Inc., Valencia, Calif., USA). Then, 1 μg of the total RNA was treated with DNase I (Invitrogen), and thereafter, cDNA was synthesized with use of Prostar first Strand RT-PCR Kit (Stratagene, La, jolla, Calif., USA). With use of 1 μg of the cDNA as a template, PCR was performed in 1 cycle of 94° C. for 2 minutes; 32 cycles of 94° C. for 30 seconds, 50° C. for 30 seconds, and 72° C. for 60 seconds; and 72° C. for 5 minutes. The primers used were the following GSH1_F7 and GSH1_R2. Used as a control was an ACT1 gene that was constitutively expressed. PCR was performed on the ACT1 with use of a primer set of ACT1F and ACT1R and the same reaction solution as that used in the above-described PCR in 1 cycle of 94° C. for 2 minutes; 30 cycles of 94° C. for 30 seconds, 55° C. for 30 seconds, and 72° C. for 60 seconds; and 72° C. for 5 minutes. The PCR product thus obtained was separated through 1.2% agarose gel electrophoresis.

```
Chem. 4
                                         (SEQ ID NO: 11)
GSH1_F7:     5'-CTTGATATGATGCTCCGAAC-3'
GSH1_R2:     5'-ATCATATAATAAACCCACCCAGAA-3'

(SEQ ID NO: 12)
ACT1F:       5'-GATGATGCACCTAGAGCTGT-3'
ACT1R:       5'-CTCCATGTCATCCCAATTGT-3'
```

Figure 2:
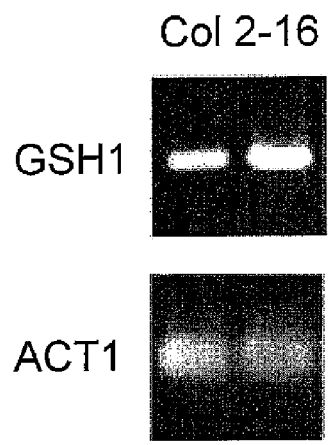
FIG. 2 shows electrophoresis images showing the results of RT-PCR performed on GSH1 mRNA obtained from a transformed plant (2-16) into which 35S-Chl.GSH1-pBI121 was introduced and on GSH1 mRNA obtained from a wild-type plant (Col), which is a parent plant of the transformed plant (2-16). Note that ACT1 is a control gene that is constitutively expressed under this growth condition.

FIG. 2 shows the result. As clearly shown in FIG. 2, it was observed that 35S-Chl.GSH1 2-16 was higher in relative mRNA amount of GSH1 than a wild type (Col-0).

Real-time PT-PCR was used to quantitatively study a GSH1 gene expression level of the transformed plant into which the 35S-cyt.GSH1-pBI121 had been introduced, in terms of total GSH1 genes including a GSH1 gene having a chloroplast targeting signal and a GSH1 gene with a deficiency of a chloroplast targeting signal, or in terms of a GSH1 gene derived from a wild-type genome (host) and a GSH1 gene introduced using the pBI121 vector. Specific steps of the real-time RT-PCR are described below.

Total RNA was extracted from aboveground parts of two-week old transformed *A. thaliana* with use of RNeasy Plant Mini Kit (Qiagen, Valencia, Calif., USA). Next, cDNA was synthesized from 1 μg of the total RNA with use of Quanti-Tect Reverse Transcription (Qiagen, Valencia, Calif., USA). Then, with use of SYBR GREEN PCR Master Mix (Applied Biosystems, Warrington, WA1 4SR, UK), real-time PCR was performed using ABI 7700. The real-time PCR was performed in 40 cycles of 50° C. for 2 minutes, 95° C. for 10 minutes, 95° C. for 15 seconds, and 60° C. for 60 seconds, by use of a reaction solution prepared from 1 μl of cDNA template, 1 μl of 20 μM forward primer, 1 μl of 20 μM reverse primer, 9 μl of H2O, and 12 μl of Master mix. Used as an internal control was 18S ribosomal RNA that is constitutively expressed. The quantity was determined from a standard curve obtained from a PCR product that was obtained by using genome DNA isolated from the wild type Col-0 as a template or by using the plasmid (35S-Chl.GSH1-pBI121) used in the transformation as a template.

Sequences of the primers used and combinations thereof, and types of detectable mRNAs are as follows:

```
Chem. 5
cyt. GSH1_7S:
5'-AATTGATTGCCGCGGCAAGTCC-3'      (SEQ ID NO: 15)

chl. GSH1_7S:
5'-CTATATATACCGCGGCGCTCTTGTC-3'   (SEQ ID NO: 16)

AtGSH1_R1:
5'-CCAGAGGCAAGATAGGCAATG-3'       (SEQ ID NO: 17)

AtGSH1_R2:
5'-CCTCACGCCACCCGAAACAA-3'        (SEQ ID NO: 18)

AtGSH1_F1:
5'-TGCGGAGAAGCTCTTGGAGATG-3'      (SEQ ID NO: 19)

AtGSH1_F2:
5'-CCGTGTTCGAAGAGCTGCTGTA-3'      (SEQ ID NO: 20)

AtGSH1_R3:
5'-TTCCGGAGACTCGAATTCTTCAG-3'     (SEQ ID NO: 21)

Nos term_R2:
5'-CCAAATGTTTGAACGATCGGGG-3'      (SEQ ID NO: 22)

18S_F:
5'-TCCTAGTAAGCGCGAGTCATC-3'       (SEQ ID NO: 23)

Figure 3:
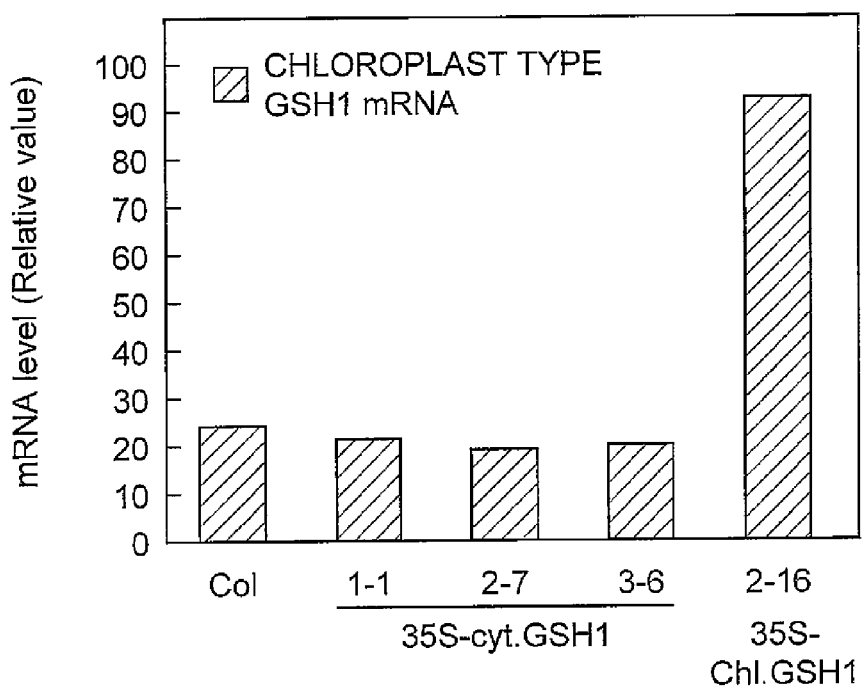
FIG. 3 is a graph showing the results of quantitative RT-PCR performed on GSH1 mRNAs having chloroplast targeting signal peptides, the GSH1 mRNAs being obtained from a wild-type plant, a transformed plant into which 35S-Chl.GSH1-pBI121 was introduced, and a transformed plant into which 35S-cyt.GSH1-pBI121 was introduced.
Figure 4:
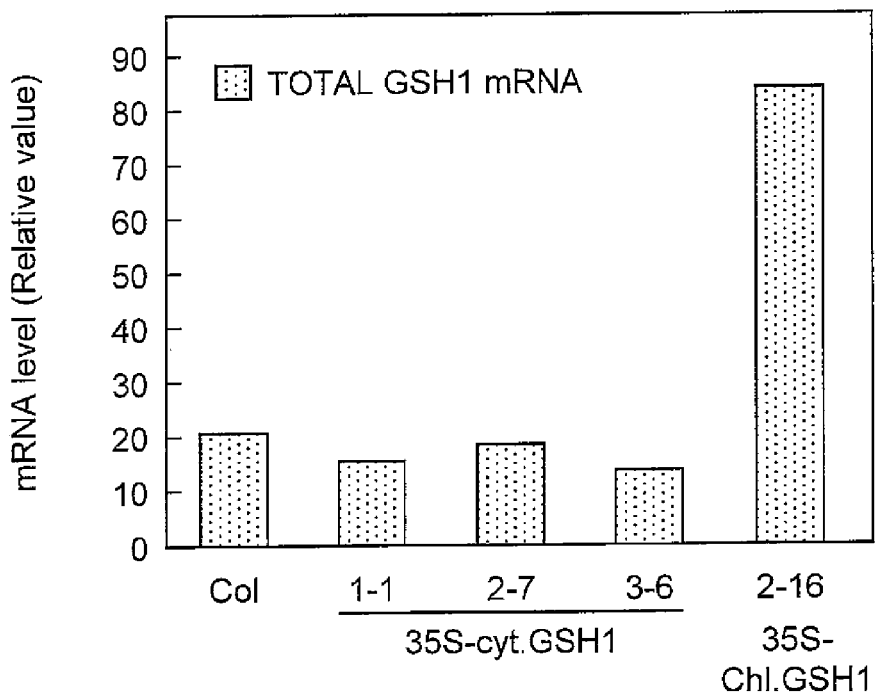
FIG. 4 is a graph showing the results of quantitative RT-PCR performed on total GSH1 mRNAs obtained from a wild-type plant, a transformed plant into which 35S-Chl.GSH1-pBI121 was introduced, and a transformed plant into which 35S-cyt.GSH1-pBI121 was introduced.
Figure 5:
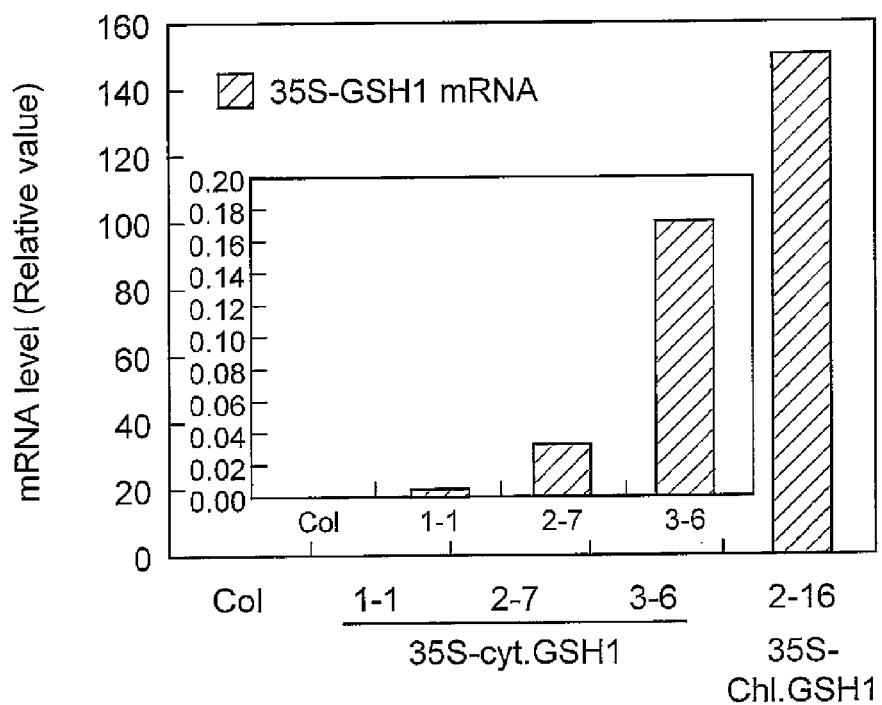
FIG. 5 is a graph showing the results of quantitative RT-PCR performed on GSH1 mRNAs obtained from a wild-type plant, a transformed plant into which 35S-Chl.GSH1-pBI121 was introduced, and a transformed plant into which 35S-cyt.GSH1-pBI121 was introduced, the GSH1 mRNAs being derived from introduced 35S-GSH1-pBI121 (35S-Chl.GSH1-pBI121 or 35S-cyt.GSH1-pBI121).
Figure 6:
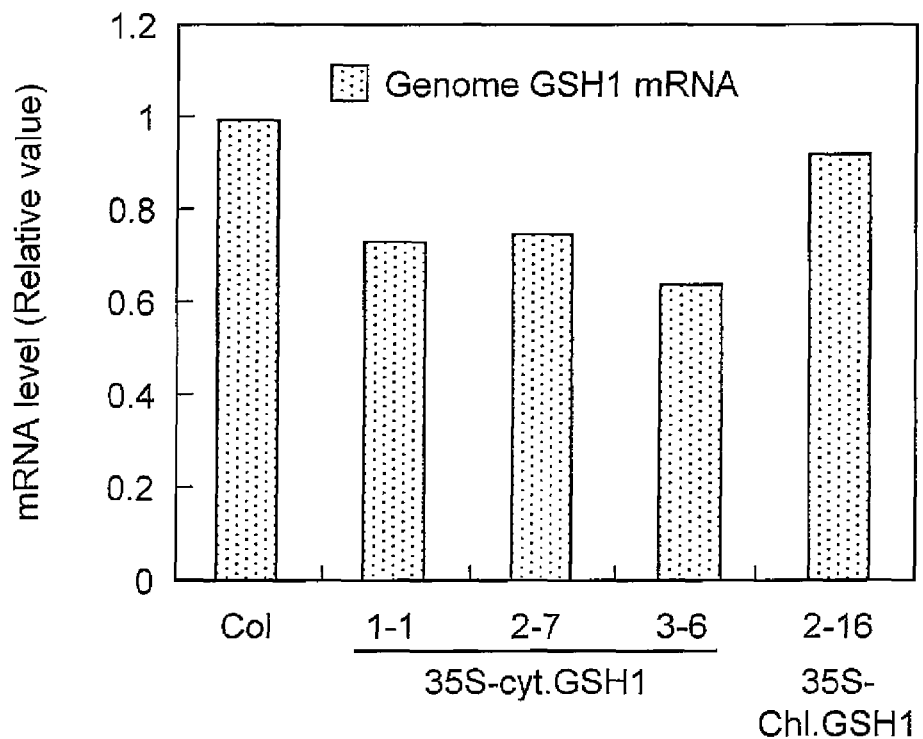
FIG. 6 is a graph showing the results of quantitative RT-PCR performed on GSH1 mRNAs derived from host genomes, the GSH1 mRNAs being obtained from a wild-type plant, a transformed plant into which 35S-Chl.GSH1-pBI121 was introduced, and a transformed plant into which 35S-cyt.GSH1-pBI121 was introduced.

18S_R:
5'-CGAACACTTCACCGGATCAT-3'        (SEQ ID NO: 24)
``` chl.GSH1__7S and AtGSH1_R2: GSH1 mRNA containing a chloroplast targeting signal
cyt.GSH1__7S and AtGSH1_R1: Total GSH1 mRNA (sum of the GSH1 mRNA containing the chloroplast targeting signal and GSH1 mRNA containing no chloroplast targeting signal)
AtGSH1_F2 and AtGSH1_R3: GSH1 mRNA derived from a host genome
AtGSH1_F1 and Nos term_R2: GSH1 mRNA derived from an introduced expression vector FIG. 3 shows expression levels of the GSH1 mRNA containing the chloroplast targeting signal. FIG. 4 shows expression levels of the total GSH1 mRNA. FIG. 5 shows expression levels of the GSH1 mRNA derived from the introduced expression vector. FIG. 6 shows expression levels of the GSH1 mRNA derived from the host genome. These figures are indicated by relative values normalized to an 18S ribosomal RNA level.

As clearly shown in FIGS. 4 and 5, the 35S-Chl.GSH1 (2-16) is higher in relative mRNA amount of GSH1 than the wild type (Col-0). On the other hand, the relative mRNA amount of the total GSH1 of the 35S-cyt.GSH1 (1-1, 2-7, and 3-6) was almost unchanged (FIG. 4). As shown in FIGS. 3 and 6, the mRNA level of the GSH1 derived from the host genome was also almost unchanged. However, as shown in FIG. 5, it was observed that the GSH1 mRNA derived from the introduced 35S-cyt.GSH1 was accumulated, albeit slightly, and found that the harvest index and the seed yield was improved (see B and C of FIG. 12).

Figure 7:
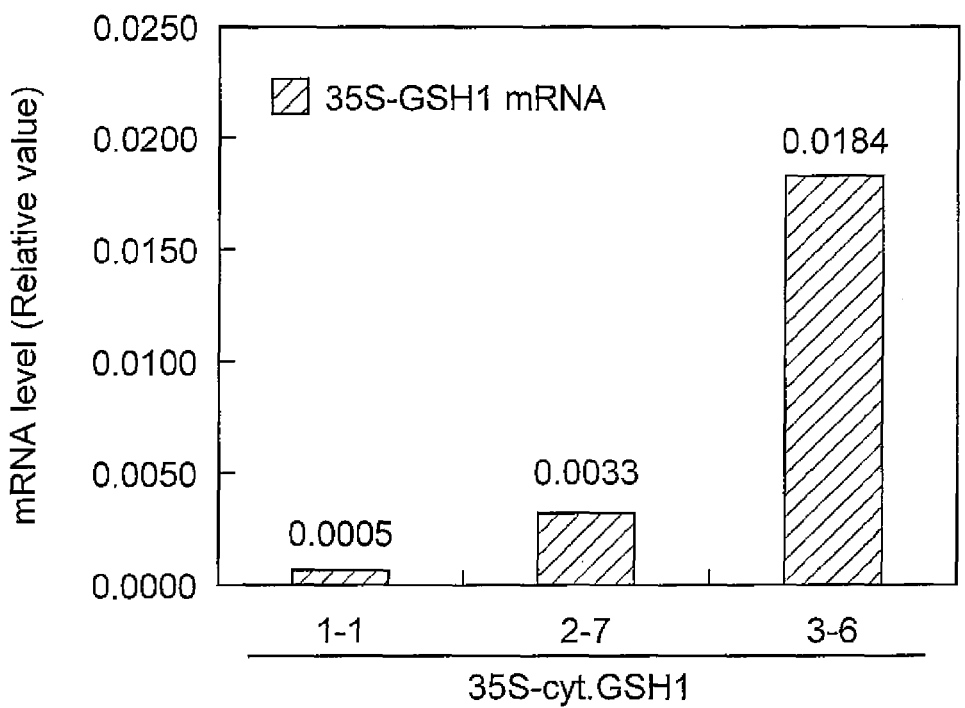
FIG. 7 is a graph showing levels of GSH1 mRNAs derived from 35S-GSH1-pBI121, the GSH1 mRNAs being obtained from transformed plants (35S-cyt.GSH1 1-1, 2-7, 3-6) into which 35S-cyt.GSH1-pBI121 was introduced. The level is indicated as a relative value, with a level of genome-derived GSH1 mRNA of a wild-type plant (Col-0) being 1.

FIG. 7 shows amounts of GSH1 mRNAs derived from the 35S-cyt.GSH1 in the 35S-cyt.GSH1 (1-1, 2-7, and 3-6), which amount is indicated as a relative value with the GSH1 mRNA amount (genome GSH1 mRNA) in the wild type (Col-0) being 1. FIG. 7 indicates that it is possible to increase the harvest index (C of FIG. 12) by expressing cytosolic GSH1 in the order of one thousandth to several tenths of the expression level of the GSH1 derived from the genome.

In order to quantitatively study the expression level of the GSH1 gene derived from a wild-type genome (serving as a host) in a T2 generation transformed plant into which the 35S-5'UTRcyt.GSH1-pBI121 was introduced and the expression level of the GSH1 gene introduced by use of the pBI121 vector, real-time RT-PCR was carried out. The T2 generation seeds were sown in an agar medium (Murashige-Skoog medium in a concentration of 50%) containing kanamycin serving as a selective marker. Next, an individual plant that exhibited kanamycin resistance was replanted in soil. After a week of growth in the soil, a leaf of the plant was picked, from which leaf total RNA was extracted. Then, cDNA was synthesized from 1 μg of the total RNA, and thereafter, real-time PCR was performed with use of SYBR GREEN PCR Master Mix (Applied Biosystems, Warrington, WA1 4SR, UK) by using ABI 7500. The real-time PCR was performed in the same manner as the above-described 35S-cyt.GSH1-pBI121.

FIG. 13 shows expression levels of the GSH1 mRNA derived from the introduced expression vector that was introduced and expression levels of the GSH1 mRNA derived from the host genome. Values in FIG. 13 are normalized to the 18S ribosomal RNA level and indicated as relative values with the GSH1 mRNA level of the 35S-cyt.GSH1(2-7) being 1. As shown in FIG. 13, the mRNA amount of the GSH1 derived from the host genome was almost unchanged (B of FIG. 13); however, the GSH1 derived from introduced 35S-5'UTRcyt.GSH1 was significantly higher in accumulation of the GSH1 mRNA than the 35S-cyt.GSH1(2-7) (A of FIG. 13). This proved that the insertion of a 5'-untranslated region of the GSH1 gene increases stability of mRNA in an individual plant. In addition, growth efficiency and productivity of these plants were improved as compared to those of the Col (FIG. 15). On the other hand, in cases where *E. coli*-derived EcGSH1 was expressed in a chloroplast (FIG. 16) and where it was expressed in cytoplasm (FIG. 17), the plants came to have shorter siliques or became sterile and, as a result, clearly decreased in seed yield.

FIG. 18 shows the harvest indices calculated by measuring aboveground biomass quantity and seed yield per individual, in a case where three individuals per pot were grown under a long-day condition (16-hour light period/8-hour dark period) at 22° C. with a light intensity of 200 μE/m$^2$/s. For an increase in harvest index, it is important to adequately select a transformant whose GSH1 gene expression level was changed by the light intensity under which it was grown. However, as clearly shown in FIG. 18, it was found that the higher GSH1 expression level the plants exhibited, the higher seed yield they exhibited at the light intensity at which they were grown.

FIG. 19 shows a relationship between (i) a planting density and (ii) growth ability and seed yield per individual, in a case where plants were grown under a long-day condition (16-hour light period/8-hour dark period) at 22° C. with a light intensity of 200 μE/m$^2$/s. A of FIG. 19 shows seed yield per individual plant. B of FIG. 19 shows differences in state among aboveground biomass quantities when the number of seeds sown per unit partition (47.25 cm$^2$) was varied. C of FIG. 19 shows variations in the aboveground biomass quantities and the seed yields when the number of seeds sown was varied. In C of FIG. 19, the graph on the left side shows variations in the aboveground biomass quantities and seed yields per individual plant, whereas the graph on the right side shows variations in the aboveground biomass quantities and seed yields per unit partition. As shown in FIG. 19, for a general plant, biomass productivity per individual decreases as a planting density of the individuals increases and, as a result, the biomass productivity per unit area levels off. FIG. 20 shows the result of comparison between a plant into which a plant-derived GSH1 has been introduced and a wild-type plant in terms of the biomass quantity and the seed yield under the above-described conditions. A and B of FIG. 20 show a case where the planting density is low (0.5 individuals per unit partition (47.25 cm$^2$)) and a case where the planting density is high (5 individuals per unit partition (47.25 cm$^2$)), respectively. In each of A and B of FIG. 20, the upper left graph shows the aboveground biomass quantity per unit partition, the upper right graph shows the seed yield, and the lower left graph shows the harvest index. Each of the graphs indicates a rate of increase with respect to the wild type Col. The graphs show that the increases in the biomass quantity and in the seed yield by the introduction of the plant-derived GSH1 become more effective in the case where the planting density is high. Such introduction of the plant-derived GSH1 gene makes it possible to effectively increase crop yield even if the crop is cultivated at a planting density increased to maximize the crop yield per unit area.

A of FIG. 21 shows a rate of increase in seed yield per unit area in the plant into which the plant-derived GSH1 gene was introduced, with respect to the wild type Col. B of FIG. 21 shows a rate of increase in total biomass quantity per unit area in the plant into which the plant-derived GSH1 gene was introduced, with respect to the wild type Col. C of FIG. 21 shows the harvest index (seed yield/total biomass quantity). FIG. 21 also reveals that the number of seeds was increased in a case where the GSH1 was expressed in cytoplasm. The average number of seeds obtainable from each individual was: 1482 for the wild type; 1486 for the 35S-chl.GSH1 2-16; 2317 for the 35S-cyt.GSH1 2-7-1; and 1815 for the 35S-cyt.GSH1 3-6-1. The rates (%) of increase for the 35S-chl.GSH1 2-16, 35S-cyt.GSH1 2-7-1, and 35S-cyt.GSH1 3-6-1 were 0.3%, 56.3%, and 22.5%, respectively, with respect to the wild type.

FIG. 22 shows a relationship between the planting density and seed yield of the wild-type plant in a case where the wild-type plant was grown under a long-day condition (16-hour light period/8-hour dark period) with the light intensity of 100 μE/m$^2$/s or 200 μE/m$^2$/s. FIG. 22 reveals that in the case of the wild-type plant, the maximum seed yield is obtained when the number of plants per unit area (47.25 cm$^2$) is 2 to 3 (the seed yield obtainable at each rate is indicated as a relative value, with the maximum value being 1). FIGS. 23 and 24 show the results obtained at the planting densities shown in FIG. 22, and reveal that the maximum value of the seed yield is increased by the introduction of the plant-derived GSH1 gene. FIGS. 23 and 24 show that this effect is enhanced in the case of a plant into which glutathione-binding aldolase (gFBA) was introduced. The plants in FIGS. 23 and 24 were grown with the light intensities of 100 μE/m$^2$/s and 200 μE/m$^2$/s, respectively. A of each of FIGS. 23 and 24 shows the seed yield per unit area, B of each of FIGS. 23 and 24 shows the total biomass quantity per unit area, and C of each of FIGS. 23 and 24 shows the harvest index. A plant in which gFBA is overexpressed was produced in accordance with the procedure described in WO2007/091634.

FIG. 25 shows the number of flowers per pot of each chrysanthemum into which the 35S-cyt.GSH1-pBI121 was introduced. Each transformant planted in 100 mL of Kureha garden cultivating soil was respectively replanted in a pot filled with 2 L of culture soil (bottom layer: 1 L of vermiculite, middle layer: 0.5 L of Kureha garden cultivating soil, top layer: 0.5 L of vermiculite), and additionally fertilized with 3 g of KUMIAI RINSHOANKARI No. S-604 every three to four weeks. The transformants were located inside a greenhouse within which the temperature was adjusted to 27° C. or higher, and bloomed under natural day length. Depending on the seedling lot and the timing at which the pot plants were repotted, the transformants were separated into four experiment groups. A and B each show the total number of flowers per pot of the transformants repotted at the end of June, whereas C and D each show the total number of flowers per pot of the transformants repotted at the end of July. As for the chrysanthemum bloomed under the natural day length, the numbers of opened flowers varied depending on the timing at which the transformants were repotted. However, it was apparent from FIG. 25 that the 35S-cyt.GSH1 plant had an increased number of flowers and that the effect of the present invention does not depend on the timing at which the plans are repotted. Note that the transformed chrysanthemums into which the 35S-cyt.GSH1-pBI121 was introduced were produced in accordance with the procedure described in www.affrc.go.jp/ja/db/seika/data_flower/h13/flower01004.html.

(4) Measurement of γ-Glutamylcysteine Synthetase (γ-ECS) Activity

An individual plant of three-week old *A. thaliana* (Col-0, 35S-Chl.GSH1 2-16) was crushed in a Tris-HCl buffer solution (pH8.0) containing 0.2 mM EDTA, 10% glycerol, and 10 mM MgCl$_2$. The solution was then centrifuged to give a supernatant. From the supernatant, low molecules were removed with use of Microcon YM-10 (Amicon, Inc., Beverly, Mass., USA). The solution thus obtained was used as enzyme solution. The enzyme solution was added to a reaction solution [120 mM HEPES (pH 8.0), 60 mM MgCl$_2$, 6 mM ATP, 6 mM PEP, 6 units pyruvate kinase, 5 mM DTE, 48 mM L-glutamate, and 40 mM L-cysteine], and then reacted at 30° C. The reaction was initiated by adding L-cysteine and terminated by adding trichloroacetic acid. After macromolecules were removed from the reaction solution with use of Microcon YM-3 (Amicon, Inc., Beverly, Mass., USA), the reaction solution was subjected to HPLC (Shiseido, Tokyo, Japan) employing a reverse-phase C18 column and model 5200A Coulochem II electrochemical detector (ESA, Inc., Chelmsford, Mass., USA) for detecting γ-EC. The HPLC used a mobile phase whose composition was as follows: 50 mM sodium phosphate monobasic monohydrate (pH 2.7), 1.0 mM octanesulfonic acid, and 2.7% methanol.

Figure 8:
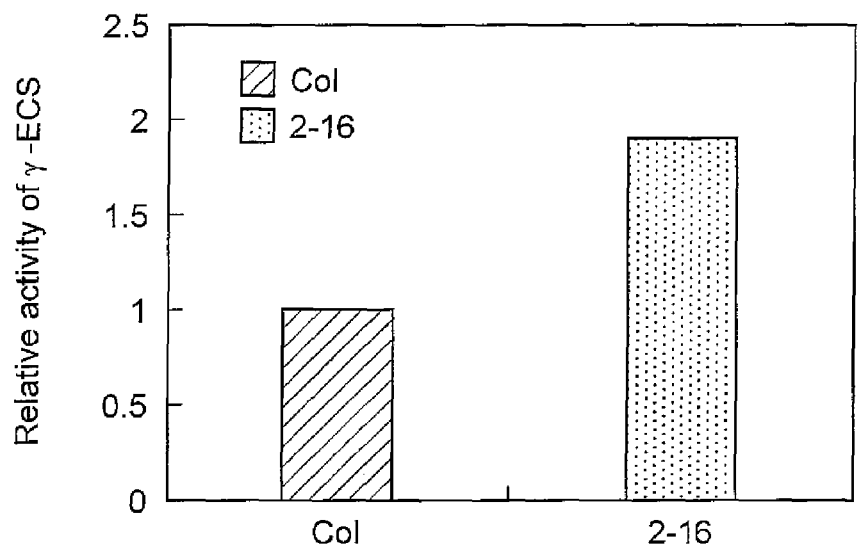
FIG. 8 is a graph showing γ-glutamylcysteine synthetase activity of GSH1 gene products obtained from a wild-type plant and a transformed plant into which 35S-Chl.GSH1-pBI121 was introduced.

FIG. 8 shows the result. It was found that the 35S-Chl.GSH1 (2-16) had twice as much GSH1 gene product γ-ECS activity as that of the wild type.

(5) Glutathione (GSH) Quantification 5-1 Method 1

Aboveground parts of three-week old *A. thaliana* (Col-0, 35S-Chl.GSH1 2-16) grown under light conditions of 25, 50, 100, 200, and 500 $\mu E/m^2/s$ were crushed in a 5% trichloroacetic acid, and then centrifuged to give a supernatant. To the supernatant thus obtained, diethyl ether of the same quantity was added so that the supernatant was suspended. Then, the ether layer was removed, and the trichloroacetic acid was removed. After repeating this operation three times, the ether was completely removed with use of a centrifugal evaporator. The resultant product was used for the measurement. The measurement was carried out by glutathione reductase-DTNB (5,5'-Dithiobis 2-nitrobenzonic acid) recycle method in accordance with Ellman's method (Ellman, G. L. (1959) Tissue sulfhydryl goups. Arch. Biochem. Biophys. 82: 70-77). The extract solution was added to a reaction solution [10 mM sodium phosphate buffer solution (pH 7.5) containing 5 mM EDTA, 0.25 mM NADPH, and 0.75 units glutathione reductase] and then 5 mM DTNB was added so as to initiate the reaction. Generation of 2-nitro-5-thiobenzonic acid was calculated from an initial rate of increase in absorbance at 412 nm. Total amount of GSH was calculated from a standard curve prepared with use of a standard substance.

Figure 9:
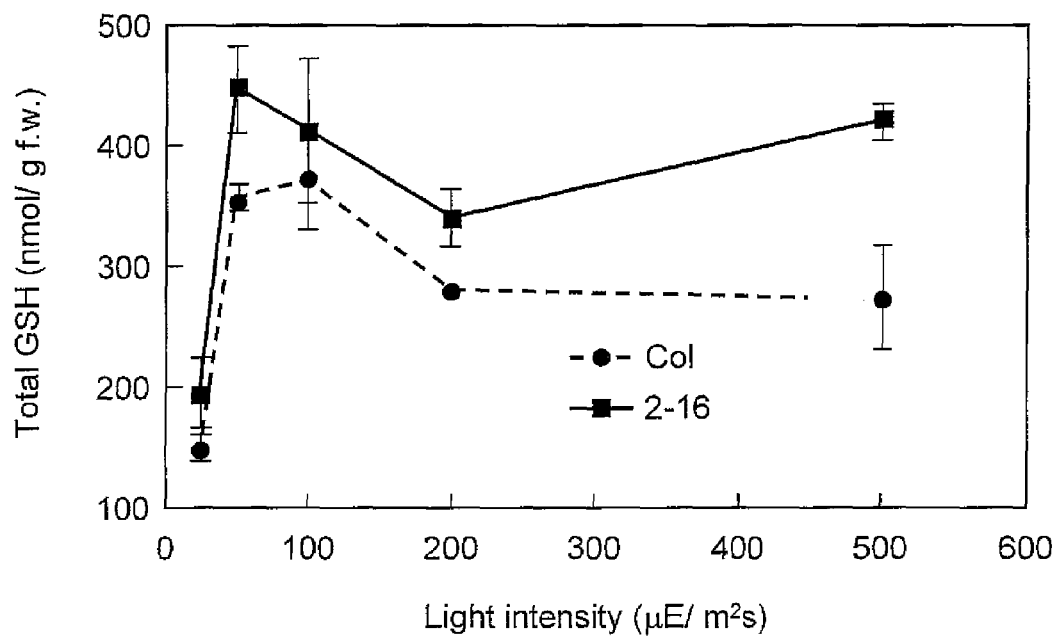
FIG. 9 is a graph showing how an endogenous glutathione level in a transformed plant into which 35S-Chl.GSH1-pBI121 was introduced was changed with variations in light intensity under which the transformed plant grows.

FIG. 9 shows the result. It was found that the 35S-Chl.GSH1 transformed plant is higher in endogenous glutathione amount than the wild type, regardless of the light intensity.

5-2 Method 2

First, aboveground parts of two-week old *A. thaliana* (Col-0, 35S-cyt.GSH1 1-1, 2-7, and 3-6) were crushed into a powder form in liquid nitrogen. Next, an extraction buffer (0.1 M HCl: (0.1 M $NaClO_4$, 0.1% $H_3PO_4$)=1:1) of the tenfold quantity of the crushed *A. thaliana* was added, then melted and mixed on ice. The mixture was centrifuged to give a supernatant. From the supernatant thus obtained, macromolecules were removed with use of Microcon YM-3 (Amicon, Inc., Beverly, Mass., USA). The supernatant was then subjected to HPLC employing a reverse-phase C18 column and LaChrom UV-VIS Detector L-7420 (Hitachi, Japan) for detecting reduced glutathione (GSH) and oxidized glutathione (GSSG). The composition of the mobile phase of the HPLC was: 0.1M $NaClO_4$, 0.1% $H_3PO_4$, and 1% acetonitrile. The amount of glutathione was calculated from a standard curve prepared with use of a standard substance.

FIG. 10 shows the result. The endogenous glutathione amount of the 35S-cyt.GSH1 transformed plant was almost the same as that of the wild type.

Figure 11:
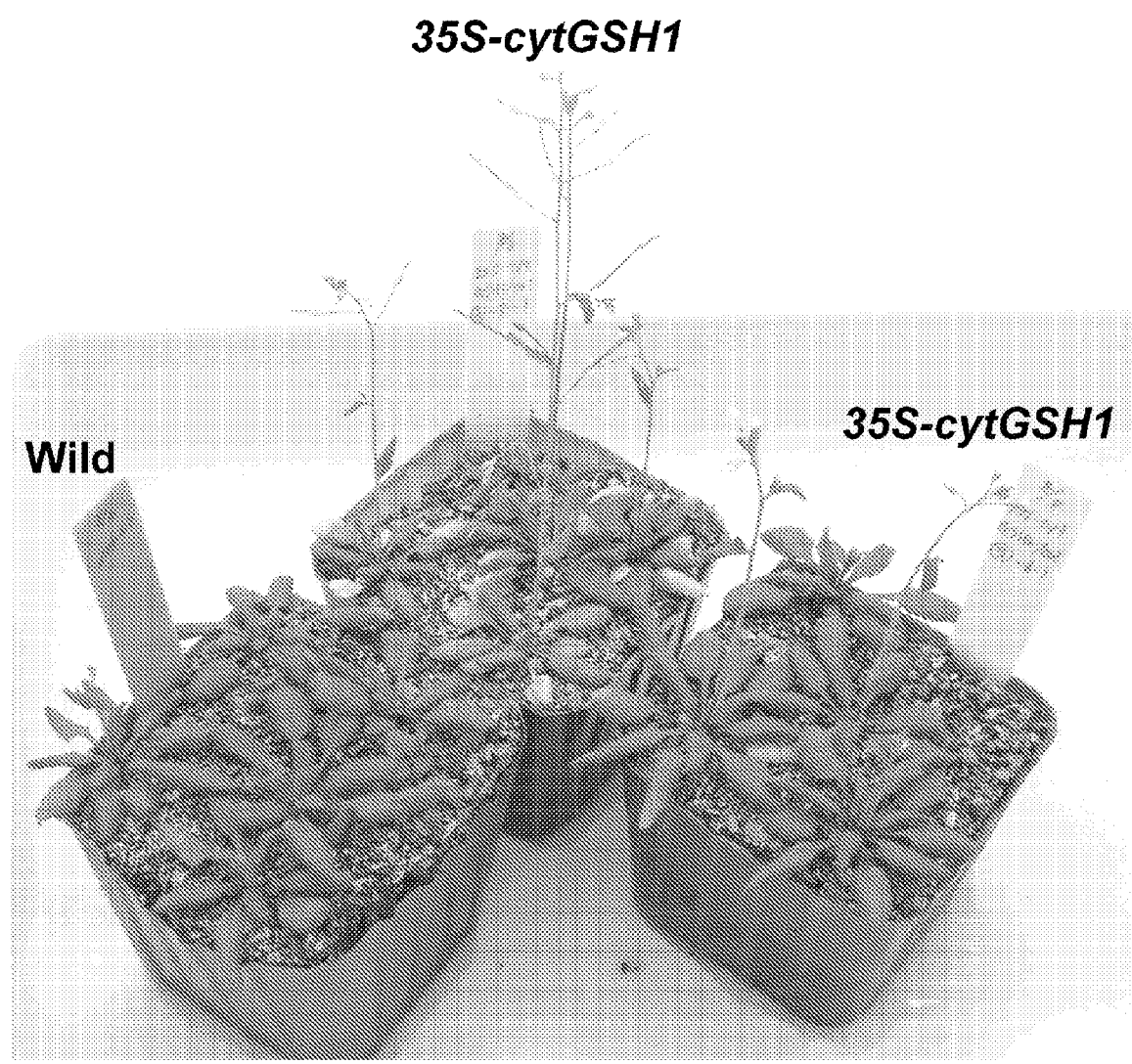
FIG. 11 is a photograph of individual plants (Col-0, 35S-cyt.GSH1) of Arabidopsis thaliana.

(6) Measurements of Seed Yield and Biomass Quantity and the Numbers of Flowers and Seeds Seeds of *A. thaliana* (Col-0, 35S-Chl.GSH1 2-16, 35S-cyt.GSH1 1-1, 2-7, and 3-6) were sown in pots, and grown under a long-day condition at 22° C. FIG. 11 shows photographs of the plant bodies of Col-0, 35S-cyt.GSH1 2-7, and 35S-cyt.GSH1 3-6. The photographs were taken on the 33rd day as counted from the day of sowing. As clearly shown in FIG. 11, the 35S-cyt.GSH1 2-7 and 35S-cyt.GSH1 3-6 were already in bloom, whereas the Col-0 was not yet in bloom. That is, FIG. 11 shows that the 35S-cyt.GSH1 transformed plants are high in growth rate than the parent plant (Col-0).

At the time when the plant individuals formed seeds at their ends of determinate inflorescence after they had bolted and bloomed, a bag was put over aboveground parts of each plant so as to collect the seeds and the aboveground parts. After the collected parts had been dried, the weight of the seeds and the weight of the aboveground parts (aboveground biomass quantity) per individual were measured.

Figure 12:
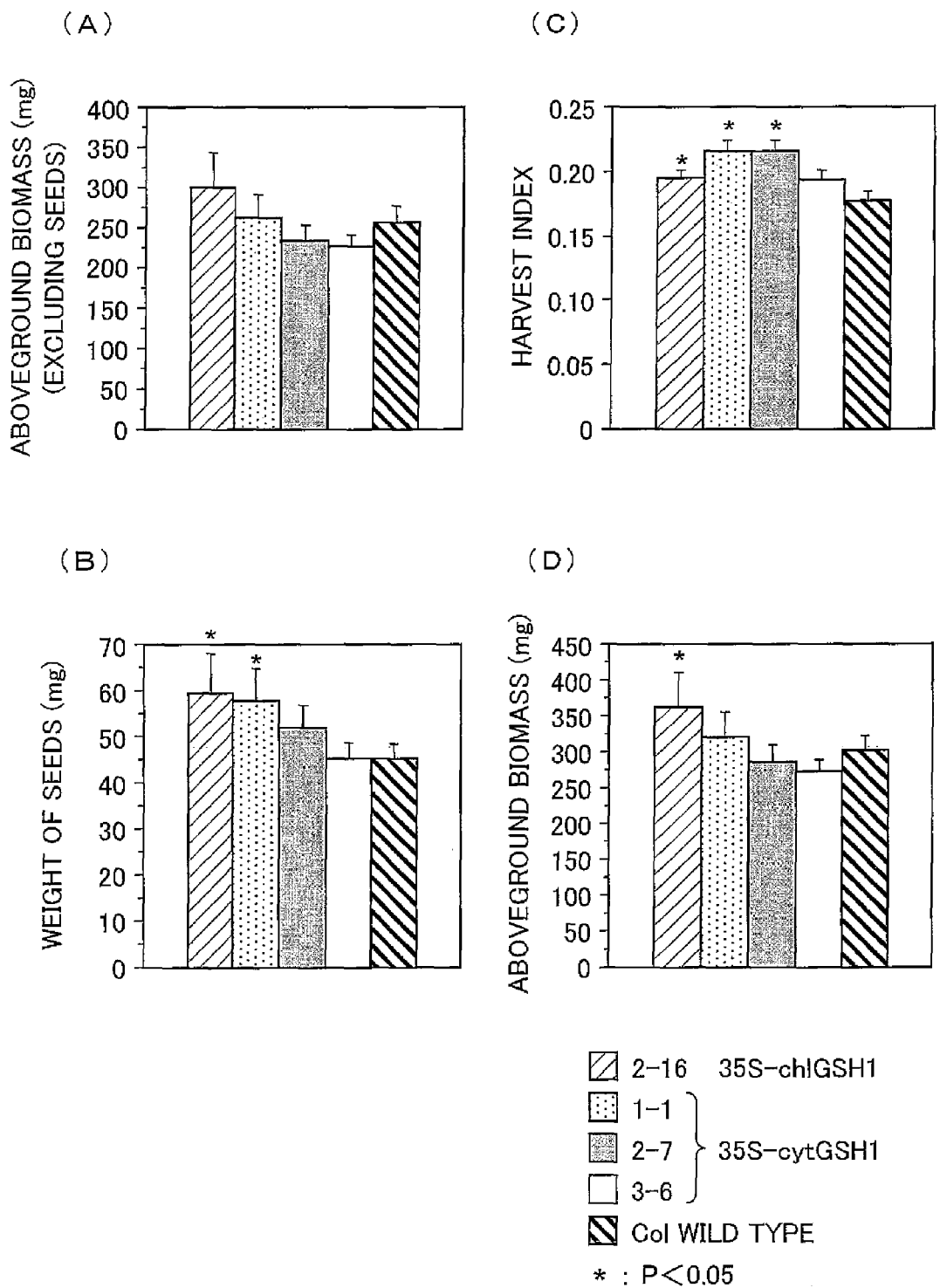
FIG. 12 shows graphs comparing Arabidopsis thaliana (Col-0, 35S-Chl.GSH1 2-16, 35S-cyt.GSH1 1-1, 2-7, 3-6) which have been grown under a long-day condition at 22° C. in terms of aboveground biomass quantity (excluding seeds) (A), weight of seeds (B), a harvest index (C), and aboveground biomass quantity (D).

A to D of FIG. 12 show the results. In FIG. 12, the asterisks indicate that the result statically has a significant difference from the Col wild type (parent plant). Specifically, the difference is considered significant if $p<0.05$ as the result of to a t-test.

A of FIG. 12 is a graph comparing aboveground biomass quantities excluding seeds. Although the 35S-Chl.GSH1 2-16 was higher in aboveground biomass quantity excluding seeds than the Col wild-type (parent plant), there was no significant difference between the two. However, as shown in D of FIG. 12, the 35S-Chl.GSH1 2-16 was significantly higher in aboveground biomass quantity including seeds than the Col wild type (parent plant). On the other hand, the biomass quantities of all of the 35S-cyt.GSH1 transformed plants were almost the same as that of the Col wild type (parent plant). B of FIG. 12 is a graph comparing the weights of seeds. The 35S-Chl.GSH1 2-16 and 35S-cyt.GSH1 1-1 were significantly higher in weight of seeds than the Col wild type (parent plant). C of FIG. 12 is a graph comparing the harvest indices. The harvest indices were each calculated by dividing the weight of seeds by the aboveground biomass quantity (excluding seeds). The 35S-Chl.GSH1 2-16, 35S-cyt.GSH1 1-1, and 35S-cyt.GSH1 2-7 were significantly higher in harvest index than the Col wild type (parent plant), while the 35S-cyt.GSH1 3-6 also exhibited an upward trend in harvest index.

The average size of the seeds of the 35S-Chl.GSH1 2-16, 35S-cyt.GSH1 3-6, 35S-cyt.GSH1 2-7, and 35S-cyt.GSH1 1-1 as compared to the Col wild type (parent plant) become smaller in this order. It was indicated, in view of the harvest index, that the number of seeds per individual of each transformed plant was greatly higher than the Col wild type (parent plant).

Since inflorescence of *A. thaliana* is structurally indeterminate, *A. thaliana* keeps forming flower buds at shoot apical meristem as long as the plant is being grown. Since the 35S-cyt.GSH1 transformed plants are high in growth rate than the parent plant (Col-0) as described above, it is indicated that the number of flowers obtainable from the 35S-cyt.GSH1 transformed plant during the same period is larger than that obtainable from the parent plant. It has been confirmed that the 35S-Chl.GSH1 transformed plant was also high in growth rate than the parent plant (Col-0), as with the 35S-cyt.GSH1 transformed plant.

The results revealed that the 35S-Chl.GSH1 transformed plant increased in the number of flowers, the number of seeds, the biomass quantity, and the weight of seeds were increased, thereby increasing in the harvest index. On the other hand, although the 35S-cyt.GSH1 transformed plant did not greatly increase in the biomass quantity, it increased in the number of flowers, the number of seeds, and the weight of seeds, thereby increasing in the harvest index.

The present invention makes it possible to increase the number of flowers and the number of seeds. As a result, it is possible to provide a productive plant having increased seed yield and harvest index.

The invention being thus described, it will be obvious that the same may be varied in many ways. Such mutations are not to be regarded as a departure from the spirit and scope of the invention, and all such modifications as would be obvious to one skilled in the art are intended to be included within the scope of the following claims.

INDUSTRIAL APPLICABILITY

The present invention makes it possible to increase the numbers of flowers or the numbers of seeds of plants. Therefore, for example, it is possible to increase the numbers of flowers and yields not only of ornamental plants and food plants, but also of woods in forests and plant resources for biomass energy. Accordingly, the present invention is applicable not only in agriculture and forestry, but also in a wide range of industries such as food industries and energy industries.

The invention claimed is:

1. A plant transformed by introducing a polynucleotide encoding a plant-derived γ-glutamylcysteine synthetase,
the polynucleotide producing a translated product having no chloroplast targeting signal peptide,
the plant being further increased in biomass quantity per unit area or seed yield per unit area in comparison with a parent plant thereof by being cultivated at a planting density higher than that which allows increases in the biomass quantity per unit area and in the seed yield per unit area
wherein the polynucleotide encoding the γ-glutamylcysteine synthetase is selected from the group consisting of the following (a) to (d):
(a) a polynucleotide encoding a polypeptide having the amino-acid sequence comprising SEQ ID NO: 3;
(b) a polynucleotide encoding a polypeptide having an amino-acid sequence in which not more than 10 amino acids of which are deleted, substituted, or added from/in/to the amino-acid sequence comprising SEQ ID NO: 3;
(c) a polynucleotide having the base sequence comprising SEQ ID NO: 4; and
(d) a polynucleotide that hybridizes, under stringent conditions, with the polynucleotide having the base sequence comprising SEQ ID NO: 4.

2. The transformed plant according to claim 1, into which a polynucleotide encoding glutathione-binding aldolase is further introduced.

3. A method for increasing the number of flowers of a plant and/or the number of seeds of the plant, the method comprising the steps of:
introducing, into the plant, a polynucleotide encoding a plant-derived γ-glutamylcysteine synthetase, wherein the polynucleotide encoding the γ-glutamylcysteine synthetase is selected from the group consisting of the following (a) to (h):
(a) a polynucleotide encoding a polypeptide having the amino-acid sequence comprising SEQ ID NO: 1;
(b) a polynucleotide encoding a polypeptide having an amino-acid sequence in which not more than 10 amino acids of which are deleted, substituted, or added from/in/to the amino-acid sequence comprising SEQ ID NO: 1;
(c) a polynucleotide having the base sequence comprising SEQ ID NO: 2;
(d) a polynucleotide that hybridizes, under stringent conditions, with the polynucleotide having the base sequence comprising SEQ ID NO: 2;
(e) a polynucleotide encoding a polypeptide having the amino-acid sequence comprising SEQ ID NO: 3;
(f) a polynucleotide encoding a polypeptide having an amino-acid sequence in which not more than 10 amino acids of which are deleted, substituted, or added from/in/to the amino-acid sequence comprising SEQ ID NO: 3;
(g) a polynucleotide having the base sequence comprising SEQ ID NO: 4; and
(h) a polynucleotide that hybridizes, under stringent conditions, with the polynucleotide having the base sequence comprising SEQ ID NO: 4; and
cultivating the plant, into which the polynucleotide is introduced, at a planting density higher than that which allows increases in biomass quantity per unit area and in seed yield per unit area.

4. A method for increasing biomass quantity or seed yield of a plant per unit area, the method comprising the steps of:
introducing, into the plant, a polynucleotide encoding a plant-derived γ-glutamylcysteine synthetase; and
cultivating the plant, into which the polynucleotide is introduced, at a planting density higher than that which allows increases in biomass quantity per unit area and in seed yield per unit area,
wherein a translated product of the polynucleotide encoding the plant-derived γ-glutamylcysteine synthetase has a chloroplast targeting signal peptide or
wherein a translated product of the polynucleotide encoding the plant-derived γ-glutamylcysteine synthetase does not have a chloroplast targeting signal peptide and a harvest index is improved.

5. The method according to claim 4, wherein the translated product of the polynucleotide encoding the plant-derived γ-glutamylcysteine synthetase has a chloroplast targeting signal peptide, and the polynucleotide encoding the γ-glutamylcysteine synthetase is selected from the group consisting of the following (a) to (d):
(a) a polynucleotide encoding a polypeptide having the amino-acid sequence comprising SEQ ID NO: 1;
(b) a polynucleotide encoding a polypeptide having an amino-acid sequence in which not more than 10 amino acids of which are deleted, substituted, or added from/in/to the amino-acid sequence comprising SEQ ID NO: 1;
(c) a polynucleotide having the base sequence comprising SEQ ID NO: 2; and
(d) a polynucleotide that hybridizes, under stringent conditions, with the polynucleotide having the base sequence comprising SEQ ID NO: 2.

6. The method according to claim 4, wherein the translated product of the polynucleotide encoding the plant-derived γ-glutamylcysteine synthetase does not have a chloroplast targeting signal peptide and a harvest index is improved, and the polynucleotide encoding the γ-glutamylcysteine synthetase is selected from the group consisting of the following (a) to (d):
(a) a polynucleotide encoding a polypeptide having the amino-acid sequence comprising SEQ ID NO: 3;
(b) a polynucleotide encoding a polypeptide having an amino-acid sequence in which not more than 10 amino acids of which are deleted, substituted, or added from/in/to the amino-acid sequence comprising SEQ ID NO: 3;
(c) a polynucleotide having the base sequence comprising SEQ ID NO: 4; and
(d) a polynucleotide that hybridizes, under stringent conditions, with the polynucleotide having the base sequence comprising SEQ ID NO: 4.

7. The method according to claim 4, further comprising the step of introducing into the plant a polynucleotide encoding glutathione-binding aldolase.

8. A method for producing a plant that is increased in biomass quantity per unit area or seed yield per unit area by being cultivated at a planting density higher than that which allows increases in the biomass quantity per unit area and in the seed yield per unit area, the method comprising the steps of:
introducing into the plant a polynucleotide encoding a plant-derived γ-glutamylcysteine synthetase; and
selecting a plant having an increased biomass or number of flowers and/or seeds in comparison with its parent plant under a cultivation condition where the planting density was higher than that which allows increases in biomass quantity per unit area and in seed yield per unit area.

9. The method according to claim 8, further comprising the step of introducing into the plant a polynucleotide encoding glutathione-binding aldolase.

10. A plant transformed by introducing a polynucleotide encoding a plant-derived γ-glutamylcysteine synthetase and further introducing a polynucleotide encoding glutathione-binding aldolase,
the polynucleotide producing a translated product having no chloroplast targeting signal peptide,
the plant being further increased in biomass quantity per unit area or seed yield per unit area in comparison with a parent plant thereof by being cultivated at a planting density higher than that which allows increases in the biomass quantity per unit area and in the seed yield per unit area.

11. A method for increasing biomass quantity or seed yield of a plant per unit area, the method comprising the steps of:
introducing, into the plant, a polynucleotide encoding a plant-derived γ-glutamylcysteine synthetase;
introducing into the plant a polynucleotide encoding glutathione-binding aldolase; and
cultivating the plant, into which the polynucleotide is introduced, at a planting density higher than that which allows increases in biomass quantity per unit area and in seed yield per unit area.

12. A method for producing a plant that is increased in biomass quantity per unit area or seed yield per unit area by being cultivated at a planting density higher than that which allows increases in the biomass quantity per unit area and in the seed yield per unit area, the method comprising the steps of:
introducing into the plant a polynucleotide encoding a plant-derived γ-glutamylcysteine synthetase; and
introducing into the plant a polynucleotide encoding glutathione-binding aldolase.

13. A plant transformed by introducing a polynucleotide encoding a plant-derived γ-glutamylcysteine synthetase, the polynucleotide producing a translated product having no chloroplast targeting signal peptide,
the plant being cultivated at a planting density higher than that which allows increases in the biomass quantity per unit area and in the seed yield per unit area,
wherein the plant having an increased biomass or number of flowers and/or seeds in comparison with its parent plant under a cultivation condition where the planting density was higher than that which allows increases in biomass quantity per unit area and in seed yield per unit area is selected.

* * * * *